(12) United States Patent
Iko et al.

(10) Patent No.: US 6,259,473 B1
(45) Date of Patent: Jul. 10, 2001

(54) SECTION IMAGE OBTAINING APPARATUS AND METHOD OF OBTAINING SECTION IMAGE

(75) Inventors: Chikaya Iko; Kunio Toshimitsu, both of Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/315,052

(22) Filed: May 20, 1999

(30) Foreign Application Priority Data

May 21, 1998 (JP) .................................................. 10-139301

(51) Int. Cl.$^7$ ................................ H04N 7/18; G06K 9/00
(52) U.S. Cl. .............................................. 348/80; 382/144
(58) Field of Search ........................ 348/79, 80; 382/144

(56) References Cited

U.S. PATENT DOCUMENTS

| | | | |
|---|---|---|---|
| 5,235,457 | * | 8/1993 | Lichtman et al. .................. 359/457 |
| 5,394,268 | * | 2/1995 | Lanni et al. .......................... 359/386 |
| 5,671,085 | * | 9/1997 | Gustafsson et al. ................. 359/385 |
| 5,801,881 | * | 8/1999 | Lanni et al. ......................... 359/386 |
| 5,932,872 | * | 8/1999 | Price ................................. 250/201.3 |

* cited by examiner

*Primary Examiner*—Chris Kelley
*Assistant Examiner*—Allen Wong
(74) *Attorney, Agent, or Firm*—Oliff & Berridge, PLC

(57) ABSTRACT

A section image obtaining apparatus includes an image-capturing device that captures an image of a subject, a section specifying device that specifies the position of a section of the subject, an image of which is to be obtained, a distance adjusting device that adjusts the distance between the subject and the image-capturing device and an image processing device that rearranges the image obtained by the image-capturing device at the position specified by the section specifying device based upon the distance that has been adjusted by the distance adjusting device.

2 Claims, 16 Drawing Sheets

SECTION IMAGE OBTAINING APPARATUS AND METHOD OF OBTAINING SECTION IMAGE

INCORPORATION BY REFERENCE

The disclosures of the following priority applications are herein incorporated by reference:

Japanese Patent Application No. 10-097927 filed Apr. 9, 1998

Japanese Patent Application No. 10-139301 filed May 21, 1998

BACKGROUND OF THE INVENTION

1. Field of the Invention

The present invention relates to a section image obtaining apparatus and a method of obtaining a section image, and in particular, it relates to a section image obtaining apparatus that employs an electronic camera for a microscope mounted at a microscope and a method adopted by the section image obtaining apparatus.

2. Description of the Related Art

The objects of examination conducted using a microscope that is to be described in this specification are specimens including cultured cells, isolated cells and sections of tissue. These specimens are examined for study of the cell internal structure in the case of a single cell, the morphological state of a cell within tissue, the morphological state of tissue constituted of a plurality of cells and the like. Examination with the microscope is conducted using two-dimensional images. The plane of such images is perpendicular to the direction of the optical axis. Thus, information along the depthwise direction is not included in such images. Information along the depthwise direction may be obtained in the manner described below through incorporation of a television camera. Images are taken in intermittently as strata images by the television camera while moving the focal position, and these images are processed at a personal computer and converted to three-dimensional images. Then, using the converted data, a three-dimensional image is produced or an image that displays the structure of a given section is created.

However, this method, in which a plurality of strata images must be taken in and processed at a computer, requires a great deal of memory capacity and also poses a problem in that a long time is required for processing.

SUMMARY OF THE INVENTION

An object of the present invention is to provide a section image obtaining apparatus provided with an electronic camera which may be mounted at, for instance, a microscope, that makes it possible to obtain a section image of a subject or a specimen within a short period of time while requiring small memory capacity and a method of obtaining a section image.

In order to attain the above object, a section image obtaining apparatus according to the present invention comprises: an image-capturing device that captures an image of a subject; a section specifying device that specifies a position of a section at the subject, an image of which is to be obtained; a distance adjusting device that adjusts a distance between the subject and the image-capturing device; and an image processing device that rearranges the image obtained by the image-capturing device at the position specified by the section specifying device based upon the distance that has been adjusted by the distance adjusting device.

A section image obtaining apparatus connected to a microscope provided with an objective lens to observe a specimen, according to the present invention, comprises: an image-capturing device that captures an image of the specimen; a section specifying device that specifies a position of a section at the specimen, an image of which is to be obtained; a distance adjusting device that adjusts the distance between the specimen and the image-capturing device; and an image processing device that rearranges the image obtained by the image-capturing device at the position specified by the section specifying device based upon the distance that has been adjusted by the distance adjusting device.

In the section image obtaining apparatus, preferably, the image-capturing device is provided with an image-capturing element achieved by two-dimensionally arraying pixels and a section image is obtained by utilizing only pixels corresponding to the position of the section specified by the specifying device.

Also preferably, an image-capturing condition setting device that sets conditions for image-capturing implemented by the image-capturing device is further provided, and the image-capturing condition setting device does not change image-capturing conditions until the image processing device completes processing corresponding to the section specified by the section specifying device.

A section image obtaining control apparatus according to the present invention, comprises: an image input unit that inputs an image of a specimen captured by an image-capturing device connected to a microscope having an objective lens that is provided to observe the specimen; a distance input unit that inputs information on the distance between the specimen and the objective lens; a section specifying device that specifies a position of a section at the specimen, an image of which is to be obtained; and an image processing unit that rearranges an image input to the image input unit at the position specified by the section specifying unit, based upon the distance information input to the distance input unit.

Another section image obtaining apparatus that obtains a section image of a subject, according to the present invention, comprises: an image-capturing device that captures an image of the subject and generates image data corresponding to the subject whose image has been captured; a section specifying device that specifies a section at the subject; a distance adjusting device that adjusts a distance between the subject and the image-capturing device in order to focus on a given position at the subject when capturing an image of the subject at the image-capturing device; and a section image processing device that processes the image data generated by the image-capturing device. And: the image-capturing device captures an image of the subject for each distance resulting from an adjustment made by the distance adjusting device; and the section image processing device extracts image data at a portion intersecting the section specified by the section specifying device among the image data generated by the image-capturing device every time an image of the subject is captured by the image-capturing device, and obtains a section image of the subject by synthesizing the image data thus extracted.

In the section image obtaining apparatus, preferably, the section image processing device is provided with a memory for synthesis that is employed to synthesize a section image and synthesizes the section image by sequentially storing extracted image data in the memory for synthesis.

Also preferably, a microscope provided with an objective lens between the subject and the image-capturing device is further provided, and the distance adjusting device adjusts the distance between the subject and the objective lens. Further preferably: the microscope enlarges an image of the subject by a magnification power of M; the image-capturing device is provided with an image-capturing element constituted of a plurality of pixels that are two-dimensionally arrayed; the distance adjusting device adjusts a distance between the subject and the section image obtaining apparatus in units of distance equalling a length of (one side of a pixel/M); and the section image processing device extracts image data at pixels corresponding to the position at which the section specified by the section specifying device is intersected. Or: the microscope enlarges an image of the subject by a magnification power of M; the image-capturing device is provided with an image-capturing element constituted of a plurality of pixels that are two-dimensionally arrayed; the distance adjusting device adjusts a distance between the subject and the section image obtaining apparatus in units of distance J; and the section image processing device extracts image data at pixels corresponding to the position at which the section specified by the section specifying device is intersected, and performs enlargement processing at a magnification power of (J/(length of one side of pixel/M)) to synthesize the extracted image data.

Also preferably: the distance adjusting device sets the distance between the subject and the image-capturing device to a specific distance; and the section specifying device specifies a single line on image data of the subject whose image has been captured by the image-capturing device at the specific distance and specifies a plane extending in a direction of an optical axis and containing the line as the section.

Also preferably: the distance adjusting device sets a plurality of distances between the subject and the image-capturing device; and the section specifying device specifies at least one point on image data of the subject whose image has been captured by the image-capturing device at each of the plurality of distances and specifies a plane containing all points that have been specified as the section.

A method of obtaining a section image of a subject, according to the present invention, comprises: a step in which a section at the subject is specified; a step in which a distance between the subject and an image-capturing device is set at an initial value; a step in which generation of image data that correspond to an image of the subject that has been captured by the image-capturing device, sequential storage of image data achieved by extracting image data corresponding to a portion intersecting the section that has been specified from the generated image data and adjustment of the distance between the subject and the image-capturing device by a specific distance are repeated; a step in which the repetition is terminated when the distance between the subject and the image-capturing device is at a final value; and a step in which the image data that have been extracted and stored in memory are synthesized to obtain a section image of the subject.

A recording medium according to the present invention records a program for obtaining a section image of a subject. The program comprises: a step in which a section at the subject is specified; a step in which an instruction is issued to set a distance between the subject and an image-capturing device to an initial value; a step in which an instruction is issued to the image-capturing device to capture an image of the subject and generate image data corresponding to the image of the subject that has been captured, the image data generated by the image-capturing device are input, image data that correspond to a portion intersecting the section that has been specified are extracted from the image data thus input and are sequentially stored in memory and an instruction is issued to adjust the distance between the subject and the image-capturing device by a specific distance in a repeated cycle; a step in which the repetition is terminated when the distance between the subject and the image-capturing device is at a final value; and a step in which the image data that have been extracted and stored in memory are synthesized to obtain a section image of the subject.

A section image obtaining apparatus that obtains a section image of a subject, according to the present invention, comprises: an image-capturing device that captures an image of the subject and generates image data corresponding to the image of the subject that has been captured; a section specifying device that specifies a section at the subject; a focal adjustment device that adjusts a focusing state in order to focus on a given position at the subject when capturing an image of the subject at the image-capturing device; and a section image processing device that processes image data generated by the image-capturing device. And: the image-capturing device captures an image of the subject for each focusing state achieved through adjustment performed at the focal adjustment device; and the section image processing device extracts image data corresponding to a portion intersecting the section specified by the section specifying device from the generated image data each time an image of the subject is captured by the image-capturing device and obtains a section image of the subject by synthesizing the image data thus extracted.

DESCRIPTION OF THE OCCURRED EMBODIMENTS

First Embodiment

The following is an explanation of the first embodiment of the present invention given in reference to the drawings.

Figure 1:
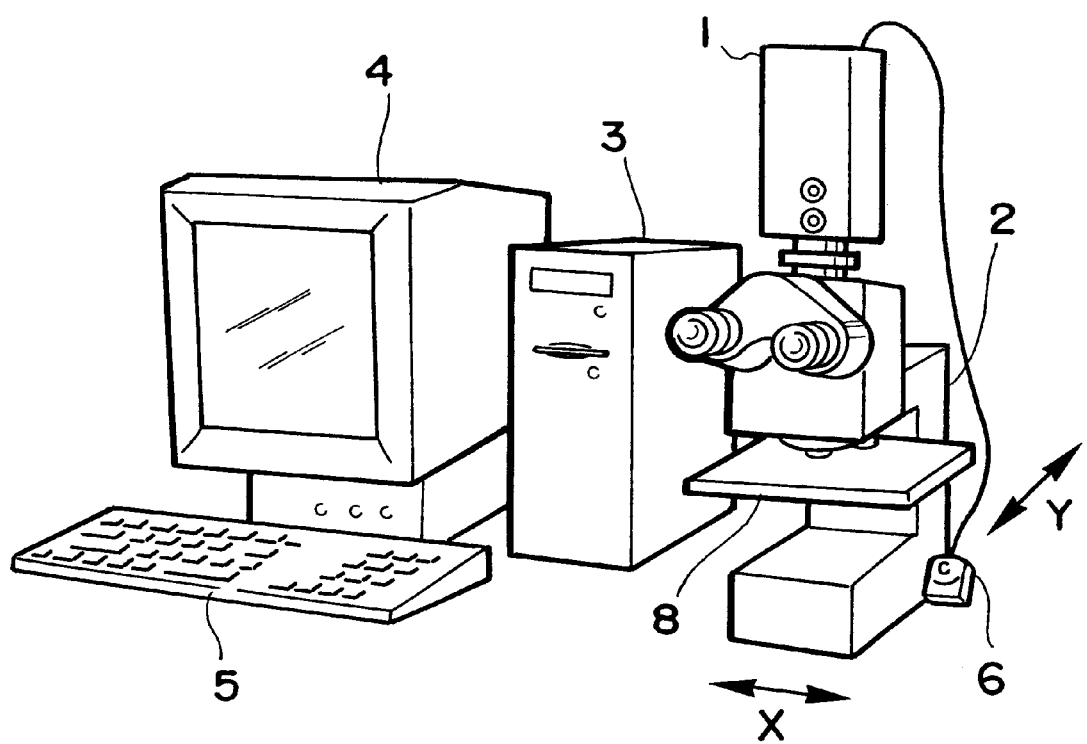
FIG. 1 is an external view of the electronic camera system in a first embodiment of the present invention.

First, in reference to FIGS. 1 through 4, the system configuration adopted in the first embodiment of the present invention is explained. FIG. 1 is an external view of the electronic camera system (section image obtaining apparatus) in the first embodiment of the present invention. This system comprises three primary units, i.e., a camera unit 1, a microscope 2 and a personal computer 3, in conformance to three separate major functions.

The camera unit 1 and the microscope 2 are mechanically connected and secured to each other via a mount (not shown). In addition, the camera unit 1 and the microscope 2 are each electrically connected to the personal computer 3.

The camera unit 1 is provided with a remote controller 6 which is electrically connected via a cable.

A monitor 4 and a keyboard 5 are electrically connected to the personal computer 3.

Figure 2:
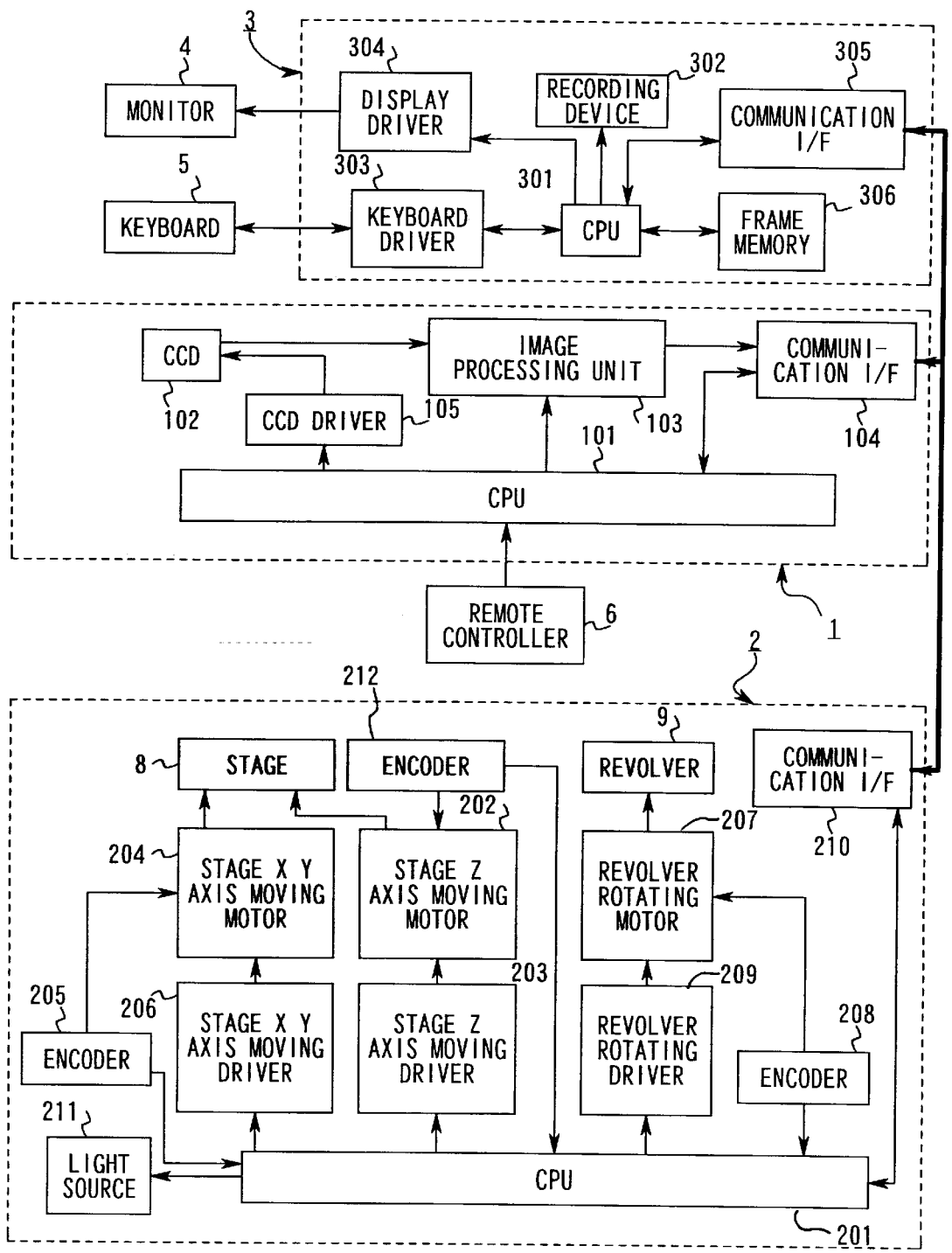
FIG. 2 is a block diagram of the electronic camera system in the first embodiment of the present invention.

FIG. 2 is a functional block diagram which illustrates the mechanical parts and the electronic parts of the electronic camera system in the first embodiment of the present invention, grouped according to the functions they provide. The following is an explanation of the individual functions fulfilled in each unit.

Figure 4:
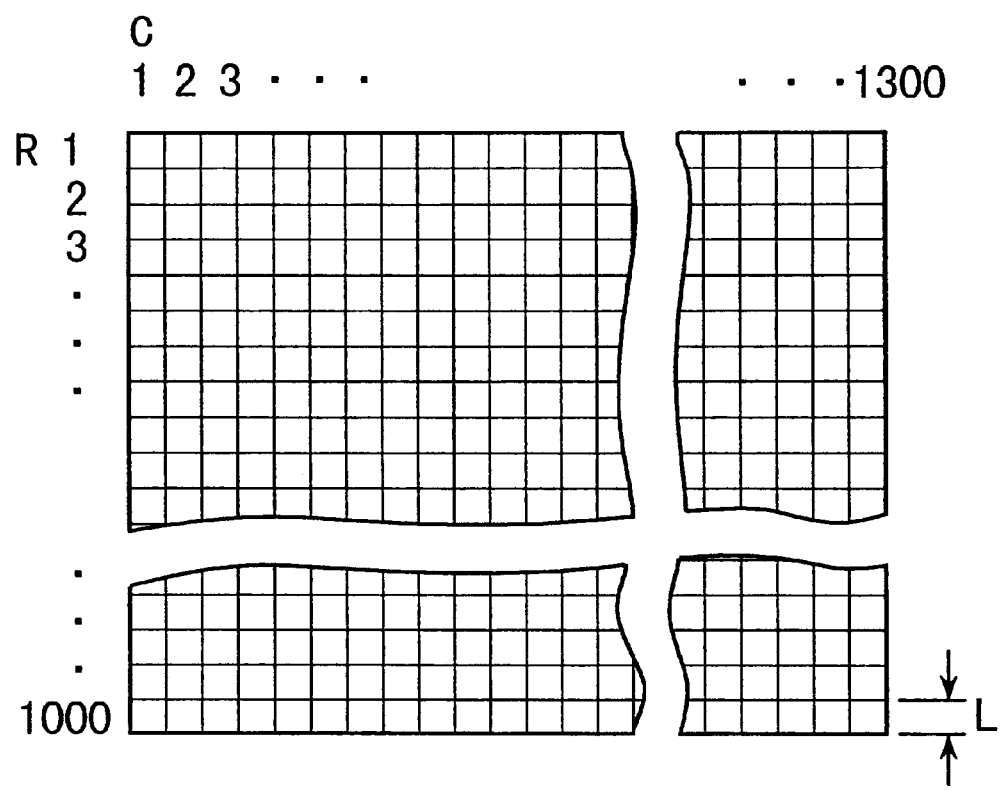
FIG. 4 illustrates the pixel array at the CCD in the first embodiment of the present invention.

First, the camera unit 1 is explained in reference to FIGS. 2 and 4.

The camera unit 1 is constituted of a so-called electronic camera. In FIG. 2, a CPU 101, which is electrically connected with various drivers and the like to be explained below, implements control of the drive at the camera unit 1.

A CCD 102 is an image-capturing element that converts an optical signal to an electrical signal. The CCD 102 is positioned so that its image-capturing plane is set at a position conjugate with the eyepiece unit to capture an image that is identical to the image examined through the eyepiece unit.

FIG. 4 illustrates the positional arrangement of effective pixels on the CCD 102. The CCD 102 is provided with 1,300,000 effective pixels to create a high-resolution screen image. In FIG. 4, 1,300 pixels are arranged in direction C, with 1,000 pixels arranged in direction R. In addition, the pixel pitch of the CCD 102 is set at 5 $\mu$m.

An image processing unit 103 performs image processing on electrical signals output by the CCD 102 to create image data in a format that can be communicated through a communication interface 104.

In addition to transferring the image data output by the image processing unit 103 to the personal computer 3, the communication interface 104 is employed in transmission/reception of various control signals with the personal computer 3 and the microscope 2. A CCD driver 105 implements control of the drive of the CCD 102 in conformance to instructions issued by the CPU 101, and controls the electric charge storage, the read timing and the like.

The remote controller 6 is operated when the user manually issues an instruction for a photographing start.

Figure 3:
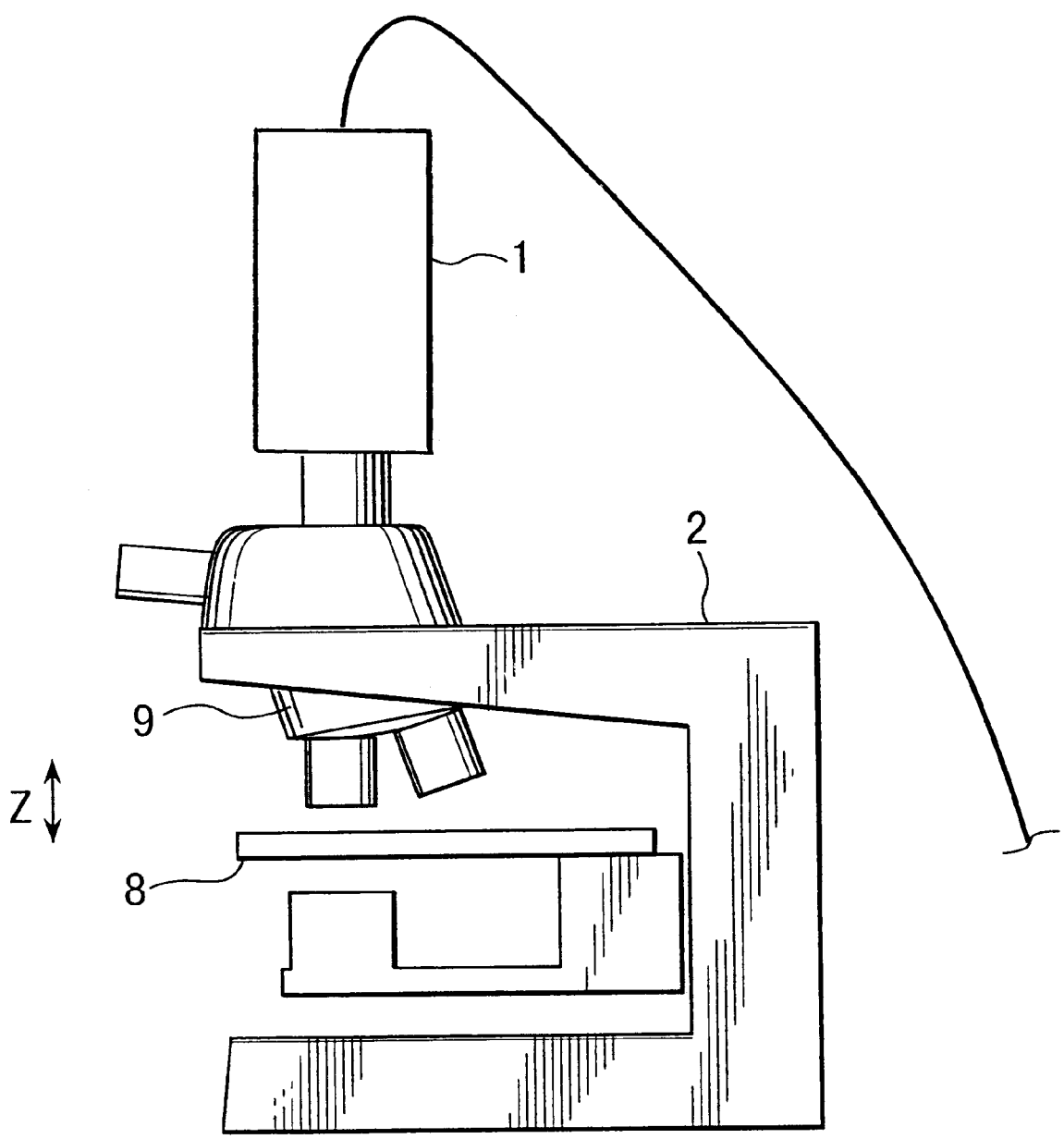
FIG. 3 illustrates the microscope employed in the first embodiment of the present invention.

Now, the microscope 2 is explained in reference to FIGS. 2 and 3.

In FIGS. 2 and 3, a CPU 201, which is electrically connected with various drivers and the like that are to be explained below, implements control of the drive at the microscope 2.

A stage Z axis moving motor 202 moves a stage 8 in the direction of the Z axis. An encoder 212, which is mechanically connected with the stage Z axis moving motor 202, indirectly detects the state of stage movement in the direction of the Z axis by detecting the rotating state of the stage Z axis moving motor 202.

A stage Z axis moving driver 203 drives the stage Z axis moving motor 202 at a specific movement pitch in conformance to instructions issued by the CPU 201. A stage X Y axis moving motor 204 moves the stage 8 in the direction of the X axis and in the direction of the Y axis. An encoder 205, which is mechanically connected with the stage X Y axis moving motor 204, indirectly detects the state of the stage in regard to its movement in the directions of the X axis and the Y axis by detecting the state of rotation of the stage X Y axis moving motor 204.

A stage X Y axis moving driver 206 drives the stage X Y axis moving motor 204 to implement movement control in conformance to instructions issued by the CPU 201.

A revolver rotating motor 207 rotates a revolver 9. An encoder 208, which is mechanically connected with the revolver rotating motor 207, indirectly detects the rotating state of the revolver 9 by detecting the state of rotation of the rotating motor 207. The CPU 201 obtains magnification power information based upon the results of the detection of the rotating state provided by the encoder 208.

A revolver rotating driver 209 drives the revolver rotating motor 207 to achieve optical variable power control in conformance to instructions provided by the CPU 201.

A communication interface 210 is electrically connected with the communication interface 104 at the camera unit 1 and a communication interface 305 at the personal computer 3 to engage in transmission and reception of various control signals.

The stage 8, on which a subject is mounted, is made to move in the direction of the X axis, the direction of the Y axis and the direction of the Z axis by the stage z axis moving motor 202 and the stage X Y axis moving motor 204.

A plurality of objective lenses having varying magnification powers are mounted at the revolver 9, and by rotating the revolver 9, the magnification power for examination is varied.

Now, the personal computer 3 is explained in reference to FIG. 2.

The personal computer 3 is internally provided with a CPU, a display driver, a frame memory and a recording device. The CPU 301 is electrically connected with the recording device 302, the keyboard driver 303, the display driver 304, the communication interface 305 and the frame memory 306, which are to be detailed later, to perform control of their drive. In addition, the CPU 301 also is employed in image processing including digital variable power (digital zoom, electronic zoom). The image processing such as digital variable power may be implemented by providing a circuit that is dedicated to image processing, instead.

Image data are recorded in the recording device 302. The recording device 302 may be constituted of a hard disk, a magneto-optical disk or the like.

The keyboard driver 303 is provided to communicate instructions input by the user through the keyboard 5 to the CPU 301. The display driver 304 generates and outputs image signals that will enable display of desired images on the monitor 4 in response to instructions issued by the CPU 301.

The communication interface 305 is electrically connected with the communication interface 104 of the camera unit 1 and the communication interface 210 of the microscope 2 and is employed to achieve transmission and reception of various control signals. In addition, the communication interface 305 receives image signals from the communication interface 104 of the camera unit 1.

The frame memory 306 is a semiconductor memory that temporarily stores image data corresponding to several frames.

The monitor 4 is a display device provided to display image signals output by the display driver 304.

The keyboard 5 is an operating device that is operated to communicate the intentions of the user to the CPU 301 via the keyboard driver 303, and more specifically, it can be used to move the cursor on the screen of the monitor 4 and to issue instructions for, for instance, a photographing start.

The following is an explanation on how the system structured as described above is employed to obtain a section image, given in reference to FIGS. 5 through 9.

Figure 5:
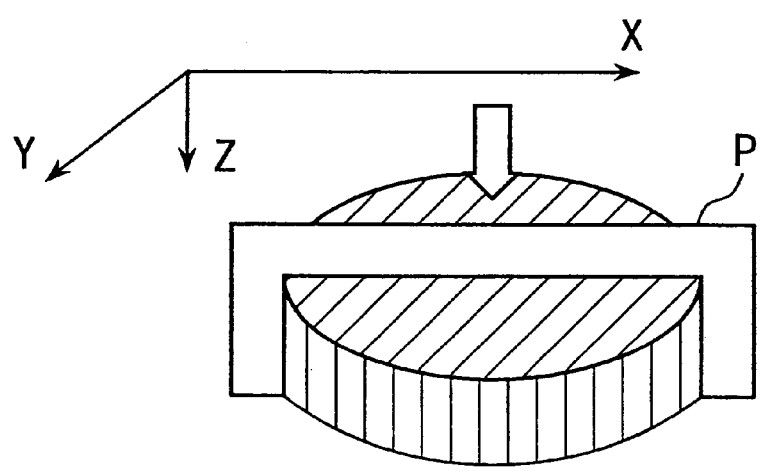
FIG. 5 illustrates a cylindrically-shaped three-dimensional specimen, a section image of which is to be obtained in the first embodiment of the present invention.
Figure 6:
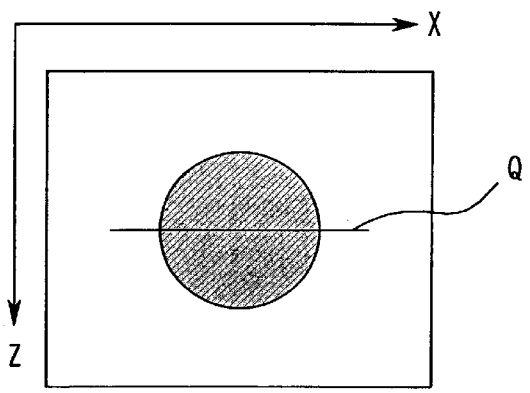
FIG. 6 illustrates the three-dimensional specimen used in the first embodiment of the present invention, viewed from the direction indicated by the arrow in FIG. 5.

FIG. 5 illustrates a cylindrically-shaped three-dimensional specimen, a section image of which is to be obtained. FIG. 6 shows an image of the three-dimensional specimen in FIG. 5 obtained by the camera unit 1 mounted at the microscope 2, viewed from the direction indicated by the arrow in FIG. 5.

Now, the method employed to obtain a section P in FIG. 5 is explained.

First, a line Q corresponding to the section P that the user wishes to obtain in the specimen is specified or designated as shown in FIG. 6. Line image data are taken in from the pixel row along the one line on the CCD 102 that corresponds to the specified section.

The line image data thus taken in are stored in the frame memory 306.

Next, the stage 8 at the microscope 2 is made to move in the direction of the Z axis by a specific movement pitch, and the focal position at the specimen is shifted to focus on the next stratum. The line image data at the stratum at the focal point are extracted and taken in, and the line image data are stored in the frame memory 306 together with information that indicates that the image follows the image whose image data have been previously stored. It is to be noted that if the section image to be obtained is elongated, with its length exceeding the length of a single frame, a memory 306 corresponding to several frames should be employed.

Figure 7:
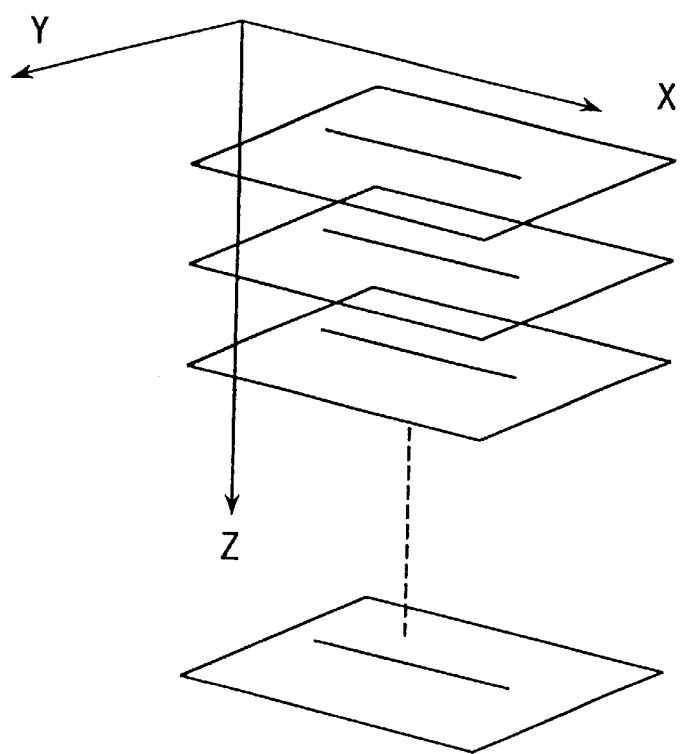
FIG. 7 illustrates the method of obtaining a section image from line image data adopted in the first embodiment of the present invention.

The process described above, i.e., the stage movement, the line image data intake and the storage, is repeated over a preset distance to obtain line image data as illustrated in FIG. 7.

When the line image data over the preset distance have been obtained, synthesizing processing is performed with the sets of line image data to create a single set of incorporated image data that constitutes one screen. Lastly, the image data having undergone the synthesizing processing are stored in the recording device.

It is to be noted that the image data attained through the method described above are an accumulation of sets of line image data that correspond to specified lines on a plurality of X Y planes cut out at a plurality of strata in the direction of the Z axis, as clearly shown in FIG. 7. In the first embodiment, the line image data at these X Y planes are regarded as line image data in the X Z plane and by synthesizing these sets of line image data, a section image is obtained.

Figure 9:
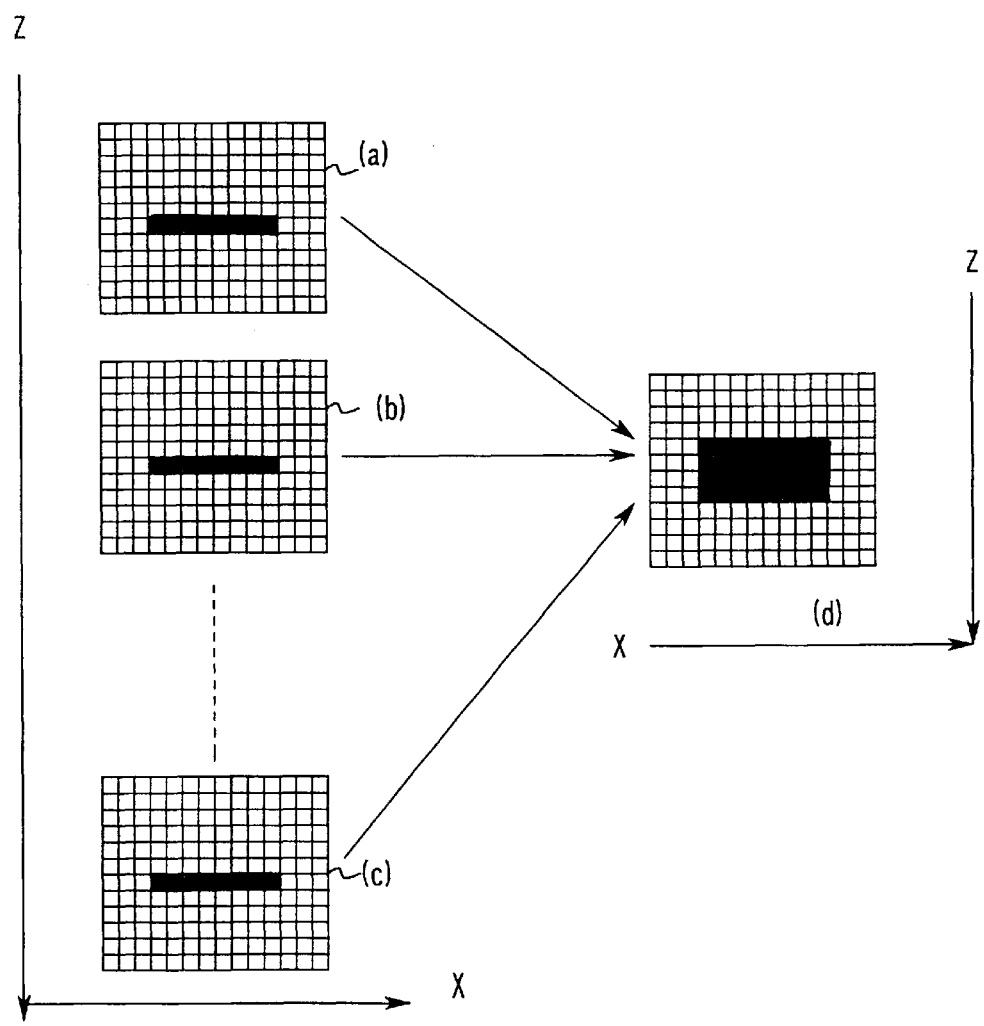
FIG. 9 illustrates the method of obtaining a section image from line image data adopted in the first embodiment of the present invention.

FIG. 9 shows the line image data obtained as illustrated in FIG. 7 and a section image achieved by synthesizing the line image data. By synthesizing the line image data in (a) through (c) in the order they have been obtained, a single section image shown in (d) is obtained.

In addition, the method of synthesizing the acquired line image data to create a section image varies depending upon the read pitch representing the width of lines taken in from the CCD and the movement pitch on the image-capturing plane of the CCD which is attributable to the movement of the stage.

The following is an explanation of the read pitch at the CCD and the movement pitch of the image-capturing plane of the CCD.

In order to match the read pitch (L) at the CCD and the movement pitch at the image-capturing plane, the movement pitch for the stage 8 must be set by ensuring that the movement pitch of the image-capturing plane is set to L. The movement pitch on the image-capturing plane of the CCD is determined in relation to the magnification power (M) achieved by the objective lenses and the relay lens and the movement pitch (S) of the stage 8.

The movement pitch (S) of the stage 8 is calculated by dividing the movement pitch on the image-capturing plane of the CCD by the magnification power (M).

$$S = L/M \qquad \text{(expression 1)}$$

However, it may not always be possible to move the stage 8 of the microscope at the movement pitch calculated through the expression above due to restrictions imposed by the moving mechanism. In a standard microscope, which is made to be electrically powered by mounting a motor at a handle that controls the vertical movement, a 0.1 μm—unit of pitch represents the minimum distance of movement of the stage 8 in the direction of the Z axis. In addition, by employing a specially designed vertical moving mechanism, a distance smaller than the above can be set for the movement. For instance, in a product that adopts a piezoelectric drive, a single pitch unit may be set to 0.01 µm.

If the stage 8 cannot be moved with the movement pitch (S) that has been calculated, a correct section image can be obtained by performing correction processing such as enlargement, reduction or the like in the direction of the Z axis while synthesizing the line images that have been obtained or after such synthesis has been completed.

If the actual stage movement pitch (J) matches the calculated stage pitch (S), a section image is obtained by simply joining or combining the obtained images.

If the obtained images are simply joined when the actual movement pitch (J) is smaller than the calculated pitch (S), the resulting section image will be elongated in the direction of the Z axis. This will necessitate correction processing through which the section image is reduced along the direction of Z axis.

When the actual movement pitch (J) is larger than the calculated pitch (S), the resulting section image will be reduced in the direction of the Z axis if the images that have been obtained are simply joined. This will necessitate correction processing through which the image is enlarged along the direction of the Z axis.

Through the following process, the correction coefficient (K) used for synthesizing is calculated using the actual stage movement pitch (J) and the calculated pitch (S) of the stage 8. The correction coefficient (K) is the numerical value obtained by dividing the actual stage movement pitch (J) by the calculated stage pitch (S).

$$K=J/S \qquad \text{(expression 2)}$$

Next, an explanation is given on a specific example of the first embodiment of the present invention. In this embodiment, the CCD illustrated in FIG. 4 with the pixel pitch at 5 µm is employed. Since only one line at the CCD is utilized, the read pitch matches the read width corresponding to one pixel at the CCD, i.e., the read pitch matches the pixel pitch.

First, an explanation is given on an application of the CCD with the pixel pitch at 5 µm employed in combination with an objective lens with a magnification power of 50 and a relay lens with a magnification power of 0.5. The relay lens is used for the following reason. Normally, the range of the visual field examined through an eyepiece lens is larger than the image-capturing plane of the CCD. Thus, in order to match the visual field of the eyepiece lens and the image-capturing plane of the CCD, a relay lens is utilized to reduce the image formed on the image-capturing plane of the CCD. For instance, when the diameter of the visual field of the eyepiece lens is 22 mm, the length of the diagonal line of the view angle of a ⅔ inch size CCD is 11 mm. In order to match these view ranges, a relay lens with a magnification power of 0.5 must be utilized since 11/22=0.5. Consequently, the product of the magnification powers of the objective lens and the relay lens is the overall magnification power which is the magnification power value (M) in expression 1.

As explained above, the read pitch (L) is equal to the pixel pitch at 5 m. By incorporating this conditional value in expression 1, $$S=5 \ \mu m/(50 \times 0.5)=0.2 \ \mu m.$$

In addition, by moving the stage at the calculated pitch 0.2 µm to obtain line image data, a section can be achieved through simple joining.

Next, an explanation is given on an application of a CCD with the pixel pitch set at 5 µm employed in combination with an objective lens with a magnification power of 40 and a relay lens with a magnification power of 0.5. Under these conditions, the stage movement pitch (S) is calculated as $$S=5 \ \mu m/(40 \times 0.5)=0.25 \ \mu m.$$

By moving the stage at the calculated pitch 0.25 µm to obtain line image data, a section image can be achieved through simple joining.

Next, an explanation is given on an application of a CCD with the pixel pitch set at 5 µm employed in combination with an objective lens with a magnification power of 100 and a relay lens with a magnification power of 0.5. Under these conditions, the stage movement pitch (S) is calculated as $$S=5 \ \mu m/(100 \times 0.5)=0.1 \ \mu m.$$

By moving the stage at the calculated pitch 0.1 µm to obtain line image data, a section image can be achieved through simple joining.

It is to be noted that when a CCD with a pixel pitch set at 5 µm, an objective lens having a magnification power of 40 and a relay lens having a magnification power of 0.5 are employed together, the stage movement pitch (S) is calculated to be 0.25 µm as explained above. This pitch cannot be matched if a standard microscope with a stage movement pitch of 0.1 µm is used. In such a case, the stage is moved by adopting the following method.

Through approximation, the value is rounded by rounding up numbers 5 and above and rounding down anything under 5 in the second digit after the decimal point so that the moving distance can be measured in units of 0.1 µm. The moving distance set through this method will not match precisely. However, it is assumed that a very slight difference in the pitch between the individual pixels will not adversely affect the appearance of a section image on display significantly. In order to move the specimen accurately, a stage which can be moved at a finer pitch as explained earlier in reference to the example will be required. However, generally speaking it can be safely assumed that the method of approximation explained above will not adversely affect the visual appearance of the section image.

Figure 10:
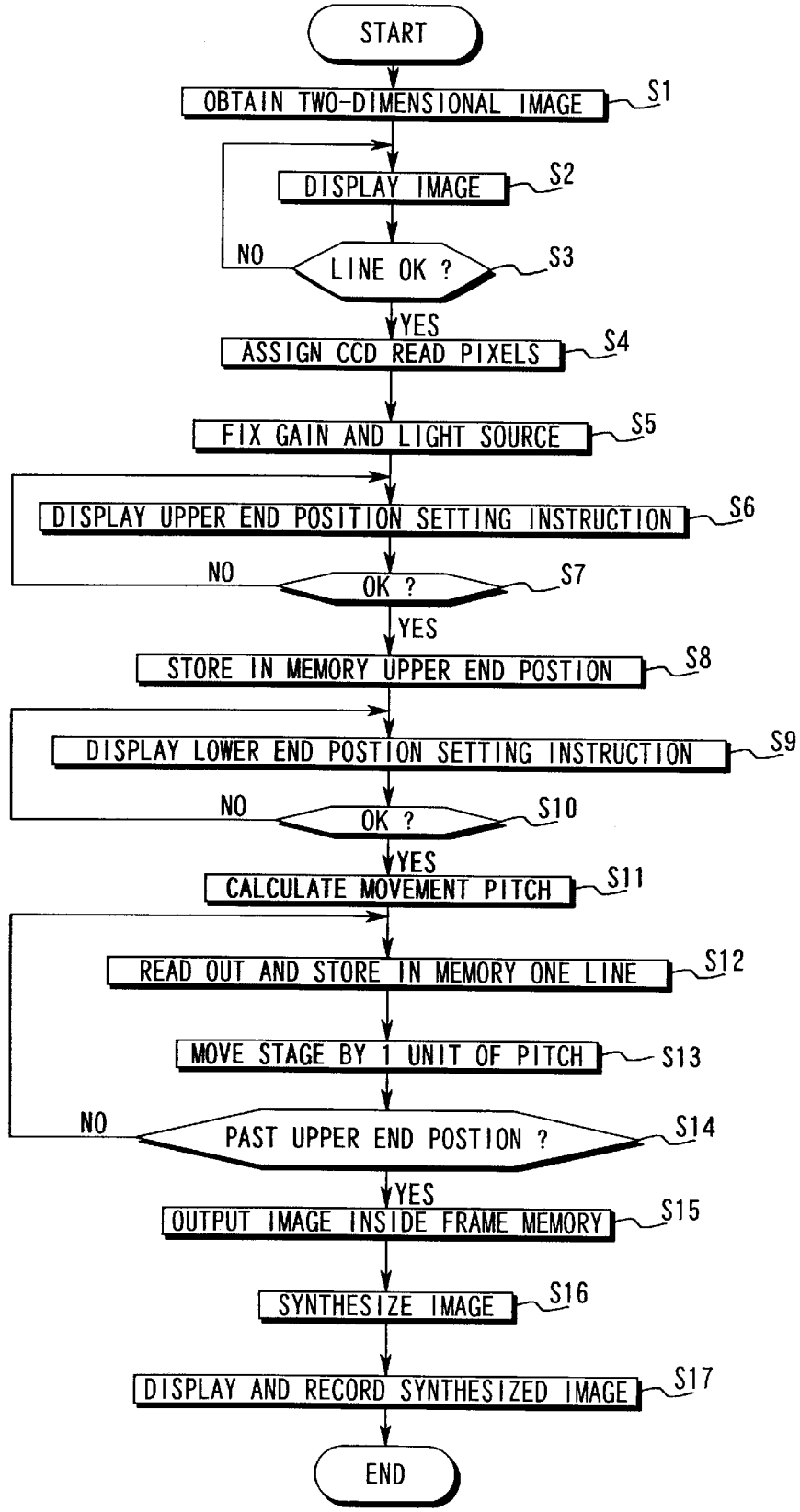
FIG. 10 is a flowchart illustrating the control achieved in the electronic camera system in the first embodiment of the present invention.

The following is a detailed explanation of the processing performed to obtain a section image, given in reference to the flowchart in FIG. 10. The processing in this flowchart starts when a section photographing mode is set. In addition, while the control implemented in the flowchart is actually achieved through job sharing among the CPU 101 at the camera unit 1, the CPU 201 at the microscope 2 and the CPU 301 at the personal computer 3. For simplification, the explanation is given on the assumption that control is achieved in a unified manner.

In FIG. 10, effective pixels at the CCD are read out and a two-dimensional image is obtained in step S1. In step S2, the two-dimensional image thus acquired, as illustrated in FIG. 6, is displayed on the screen of the monitor 4.

In step S3, the line Q is input by adopting a method to be detailed later and a decision is made as to whether or not an okay has been granted. If it has been okayed, the operation proceeds to step S4, whereas if an okay has not been granted, the operation returns to step S2.

A section achieved by cutting across the line Q input in this step will be obtained. Now, the method of inputting the line Q, i.e., the method employed to specify a desired section, is explained. A line in the lateral direction, as illustrated in FIG. 6, or a line in the longitudinal direction may be specified by placing or superimposing the cursor at a position on the monitor screen while observing the specimen on the screen of the monitor 4. Namely, a horizontal or vertical cursor for section position specification is displayed on the monitor 4, the line is moved by inputting instructions via the arrow keys on the keyboard or by dragging the mouse and the line is set at a desired position.

In addition, instead of the lateral or longitudinal direction, specification may be made in any diagonal direction. In that case, the specification can be made by specifying two points on the screen.

In step S4, specific pixels at the CCD 102 that are to be used in correspondence to the input line Q are assigned. For instance, the pixels through which the line Q passes may be assigned as operating pixels. If the line Q extends parallel to the array of pixels, the pixels over a specified range, along one line in the lateral direction or one row along the longitudinal direction are assigned. If the specified line Q extends diagonally, either all the pixels through which the line Q passes are assigned or pixels that are selected by specific criteria are assigned. In this case, the maximum number of pixels to be assigned is the entire number of pixels through which the line Q passes. The pixels assigned in this manner are those at positions corresponding to the positions where the section cut across the line Q and the two-dimensional image obtained by the CCD 102 intersect. It is to be noted that the line Q may have a width equivalent to several pixels to support color images.

In addition, while the pixels at the CCD 102 that correspond to the line are assigned as operating pixels in this explanation, pixels that are to be used may be assigned in advance and made to correspond to the specified line Q by moving the stage 8 along the X axis and the Y axis.

In step S5, the output gain of the CCD 102, the brightness of the light from a light source 211, the white balance and the like are determined and fixed. When line image data are obtained in step S12 explained later, the values set in this step are used. This ensures that a consistent and even section image is achieved.

In step S6, a display for issuing an instruction to specify the upper end position of a section to be obtained is brought up on the screen of the monitor 4.

Figure 11:
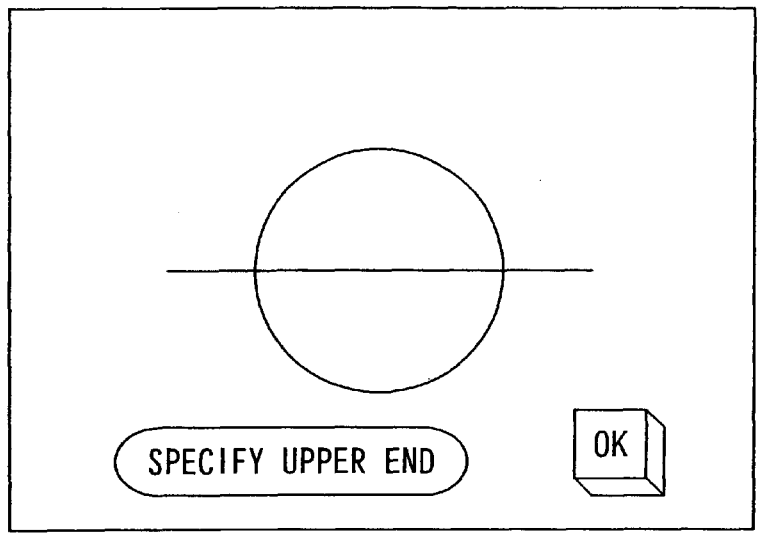
FIG. 11 illustrates an example of display on the monitor screen in the first embodiment of the present invention.

At this point, prompted by the display shown in FIG. 11, the user moves the stage 8 in the direction of the Z axis while observing the specimen and stops the stage 8 at the position at which the upper end of the specimen whose section is to be obtained is in focus (this position is referred to as the upper end position). Then the user inputs "OK" on the screen.

In step S7, a decision is made as to whether or not "OK" in the screen display shown in FIG. 11 has been input, and the operation proceeds to step S8 if "OK" has been input, whereas the operation returns to step S6 if it has not been input.

In step S8, the position of the stage 8 at the time point at which "OK" has been input in step S7 is stored in memory as the upper end position.

In step S9, a display for issuing an instruction to specify the lower end position of the section to be obtained is brought up on the screen of the monitor 4.

Figure 12:
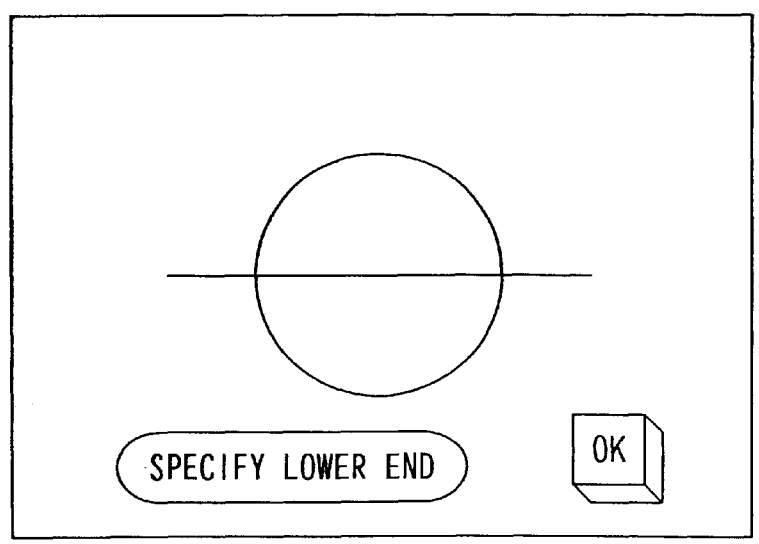
FIG. 12 illustrates an example of display on the monitor screen in the first embodiment of the present invention.

At this point, prompted by the display shown in FIG. 12, the user moves the stage 8 in the direction of the Z axis while observing the specimen and stops the stage 8 at the position at which the lower end of the specimen whose section image is to be obtained is in focus (this position is referred to as the lower end position). Then the user inputs "OK" on the screen.

In step S10, a decision is made as to whether or not "OK" in the screen display shown in FIG. 12 has been input, and the operation proceeds to step S11 if "OK" has been input, whereas the operation returns to step S9 if it has not been input.

In step S11, the movement pitch at which the stage 8 is moved is calculated through the calculation method explained earlier.

In step S12, line image data are output from the assigned pixels within the CCD 102 and the line image data are stored in the frame memory 306.

The line image data corresponding to the assigned pixels may be obtained in this step either by reading out only the assigned pixels within the CCD 102 or by reading out all the effective pixels and extracting only the signals corresponding to the assigned pixels.

In step S13, the stage 8 is caused to move toward the upper end by one unit of pitch at the pitch calculated in step S11.

In this step, the stage 8 is made to move automatically from the lower end position at which the objective lens and the specimen are the closest to each other toward the upper end position at which the objective lens and the specimen are far away from each other, to prevent the objective lens and the specimen from coming into contact with each other even if, after the stage starts to move, it should travel beyond the stop position due to a mechanical error, a software error or the like.

In step S14, a decision is made as to whether or not the position of the stage 8 is beyond the upper end position stored in memory in step S8, and if it is decided that the position is beyond the upper end position, the operation proceeds to step S15, whereas the operation otherwise returns to step S12.

In step S15, all the images stored in the frame memory 306 are output. In step S16, image processing is performed on the output images by adopting the correction method explained earlier to produce a single section image through synthesis.

Figure 8:
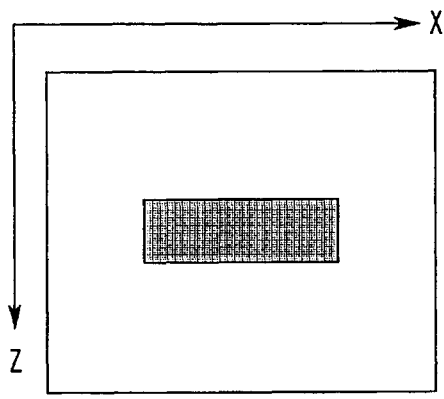
FIG. 8 illustrates the method of obtaining a section image from line image data adopted in the first embodiment of the present invention.

In step S17, a synthesized image as illustrated in FIG. 8 is displayed on the screen of the monitor 4 and is recorded in the recording device 302.

Second Embodiment

Next, the second embodiment of the present invention is explained.

The second embodiment explained below differs from the first embodiment in the method of specifying the section to be obtained and the method of assigning pixels in the CCD 102. Since other features of the second embodiment are identical to those of the first embodiment, the explanation of the identical features is omitted.

Figure 13:
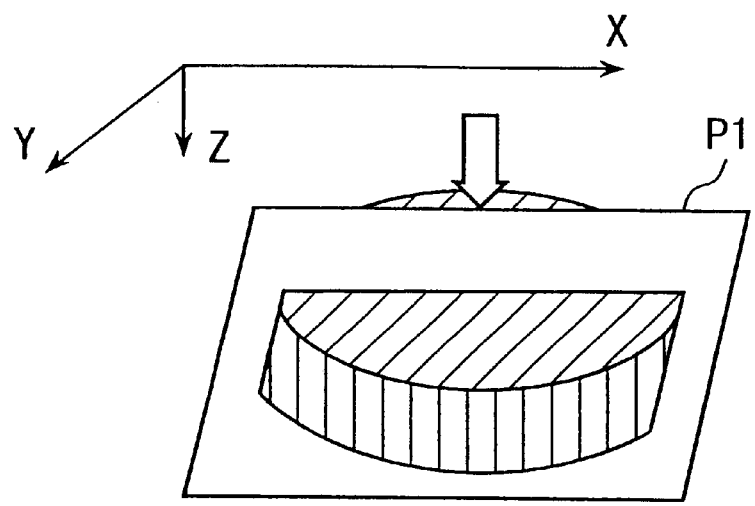
FIG. 13 illustrates a cylindrically-shaped three-dimensional specimen, a section image of which is to be obtained in a second embodiment of the present invention.

FIG. 13 shows a cylindrically-shaped three-dimensional specimen, a section of which is to be obtained.

Figure 14:
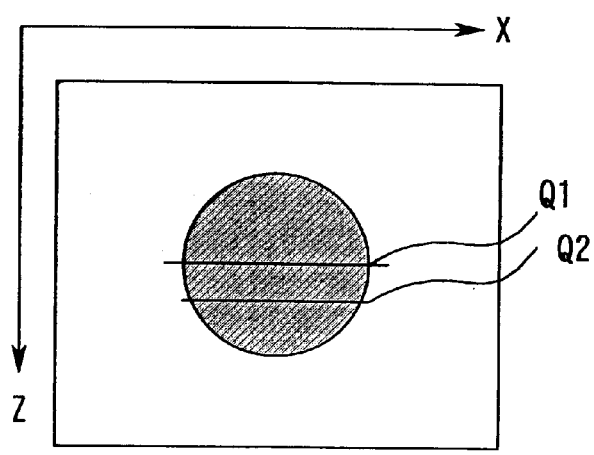
FIG. 14 illustrates the three-dimensional specimen used in the second embodiment of the present invention, viewed from the direction indicated by the arrow in FIG. 5.

FIG. 14 shows an image of the three-dimensional specimen in FIG. 13 obtained by the camera unit 1 mounted at the microscope 2, and viewed from the direction indicated by the arrow in FIG. 13.

Figure 15:
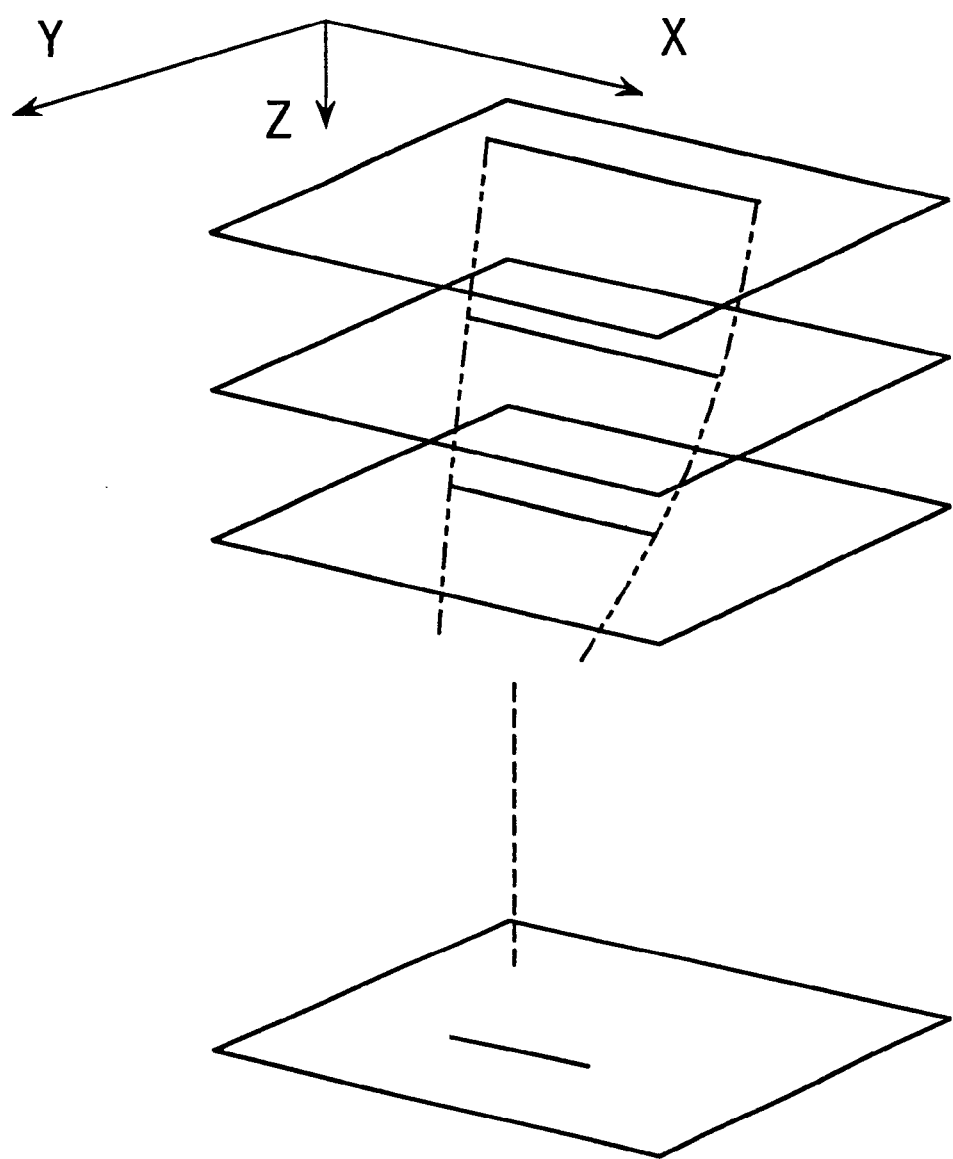
FIG. 15 illustrates the method of obtaining a section image from line image data adopted in the second embodiment of the present invention.
Figure 16:
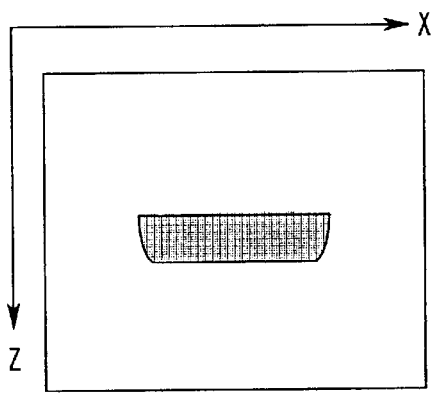
FIG. 16 illustrates the method of obtaining a section image from line image data adopted in the second embodiment of the present invention.
Figure 17:
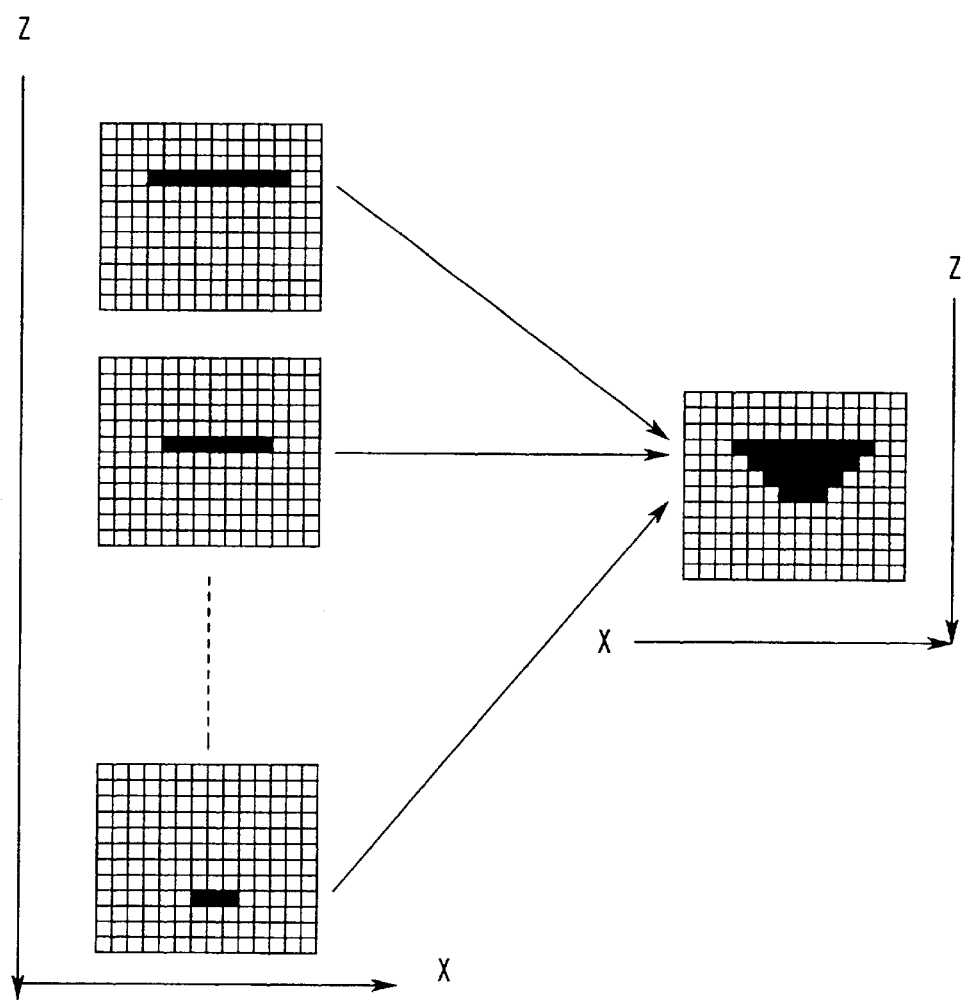
FIG. 17 illustrates the method of obtaining a section image from line image data adopted in the second embodiment of the present invention.

FIGS. 15, 16 and 17 respectively correspond to FIGS. 7, 8 and 9 illustrating the first embodiment.

When capturing the internal structure of tissue or a cell in a specimen, it may be desirable to obtain a section such as the section P1 illustrated in FIG. 13 along a direction extending at an angle relative to the Z axis. For instance, it may be necessary to obtain a section along a direction selected in conformance to the position at which the nucleus within the cell in the specimen is located and the shape of the cell or along a direction selected in conformance to the internal structure of the tissue. In FIG. 14, line Q1 indicates the cutting edge at the upper surface and line Q2 indicates the cutting edge at the lower surface, of the specimen cut along the section P1 in FIG. 13.

The following is an explanation of the method of specifying the lines Q1 and Q2 in FIG. 13. In steps S2 and S3 in the first embodiment, illustrated in the flowchart in FIG. 10, only one line at the upper surface of the specimen is specified. In the second embodiment, one line at the specimen upper surface and one point at the specimen lower surface are specified by placing the cursor on the monitor screen. Alternatively, three points may be specified.

In either case, a desired section is specified by specifying a straight line and one point or by specifying three points for one surface.

The following is an explanation of the method for assigning pixels in the CCD 102. In the first embodiment, a section image is obtained using only the assigned pixels at the CCD 102. In the second embodiment, since the section to be obtained is at an angle relative to the Z axis, the pixels that correspond to the specified section change as the stage 8 moves in the direction of the Z axis. Thus, in the second embodiment, the operating pixels in the CCD 102 that change in conformance with movement of the stage 8 are assigned in correspondence to the movement of the stage 8 in step S4 in the flowchart shown in FIG. 10, and in step S12, a read out is performed from the pixels that have been assigned in correspondence to the movement of the stage 8.

Other structural features and aspects of control are identical to those in the first embodiment explained earlier.

Figure 18:
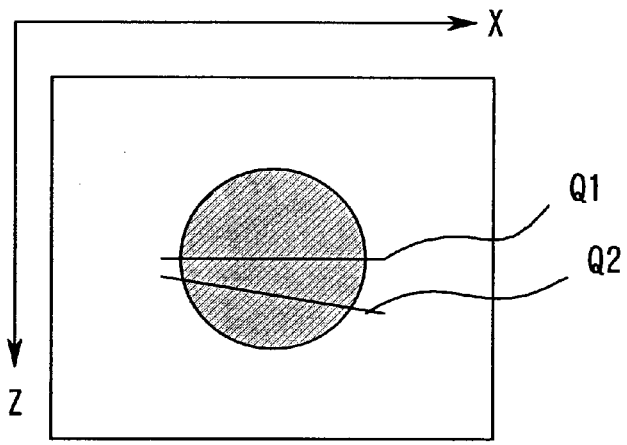
FIG. 18 illustrates the three-dimensional specimen used in the second embodiment of the present invention, viewed from the direction indicated by the arrow in FIG. 5.
Figure 19:
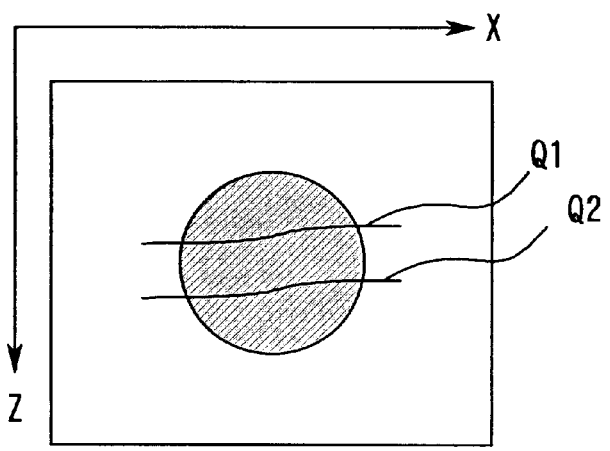
FIG. 19 illustrates the three-dimensional specimen used in the second embodiment of the present invention, viewed from the direction indicated by the arrow in FIG. 5.

In addition, in the second embodiment, a section image which is cut along lines Q1 and Q2 which are not parallel to each other as illustrated in FIG. 18 or a section image that is cut using lines Q1 and Q2 that are curved as illustrated in FIG. 19, can be obtained.

As explained above, in this embodiment, instead of obtaining a plurality of two-dimensional strata images on the X Y planes cut out at a plurality of strata along the direction of the Z axis in order to obtain a section image on the X Z plane, line image data corresponding to the area related to the section to be obtained among the individual strata images are obtained so that a section image can be created at high speed.

It is to be noted that while the user sets the upper end position and the lower end position of the specimen in the first embodiment and in the second embodiment explained above, the upper end position and the lower end position of the specimen may be automatically detected and set through image analysis. In this case, it is conceivable that the objective lens may come in contact with the specimen depending upon the height of the specimen. In order to ensure that this does not happen, it should be stopped at a specific value even when the upper end position or the lower end position of the specimen has not been detected.

Alternatively, a pre-scan may be performed in advance to ascertain the height, the brightness and the like of the specimen before an operation to obtain a section image is executed.

In addition, a one-dimensional CCD, instead of a two-dimensional CCD may be employed. Such a CCD may be employed to obtain a one-dimensional section by acquiring two-dimensional images on X Y planes with the stage 8 caused to move in the direction of the X axis or the Y axis when acquiring two-dimensional images.

In the first and second embodiments, the line image data are stored in the frame memory 306 while the image acquisition is in progress, and when all the line image data have been obtained, the synthesizing processing is implemented to record the data as a single image. However, the synthesizing processing may be implemented each time line image data are obtained.

While data at the assigned pixels corresponding to a specific single line are output at an image-capturing element capable of outputting data in units of pixels corresponding to individual lines, a regular CCD is not capable of outputting data from pixels corresponding to a single line and for this reason, after reading out all the effective pixels in the CCD, data other than the data corresponding to the one line may be discarded.

In addition, while a monochrome image is output using one line at the CCD having color filters arranged in a Bayer array in the first embodiment and in the second embodiment, a color section image can be obtained by using two lines instead and implementing interpolation processing.

Furthermore, when a two-dimensional CCD is employed as in the first embodiment and in the second embodiment, a plurality of section images may be obtained by simultaneously acquiring line image data corresponding to pixel rows over a plurality of lines that are in the same vicinity or corresponding to pixel rows over a plurality of lines that are away from one another over a specific number of pixels instead, to store the best section image among them. It is to be expected that when the intent is to obtain a plurality of section images, a plurality of lines may be specified to obtain a plurality of section images.

While automatic control is implemented for the movement of the stage 8 on the X Y plane and for the movement of the Z axis toward the focal point in the first embodiment and the second embodiment, the control may be achieved manually by referring to the vernier indicating the stage X Y position and the markings on the Z axis adjusting knob.

While the explanation has been given in reference to the first embodiment and the second embodiment on examples in which the focus position for the specimen is adjusted by moving the stage 8 along the direction of the Z axis, the present invention is not limited to the details of these examples. For instance, a mechanism that automatically adjusts the position of the objective lens of the microscope in the direction of the Z axis may be provided so that an image is captured by focusing on an arbitrary position of the specimen to obtain a section image. In addition, the present invention may be adopted in applications in which no microscope is used. For instance, when there are a camera and a transparent subject, the focal adjustment mechanism at the camera may be adjusted to focus at an arbitrary position of the subject for image-capturing to obtain a section image of the subject. In this case, too, it goes without saying that the focus position on the subject may be changed by employing a mechanism that varies the distance between the camera and the subject.

Third Embodiment

Now, the third embodiment of the present invention is explained in reference to FIGS. 20 through 23.

Figure 20:
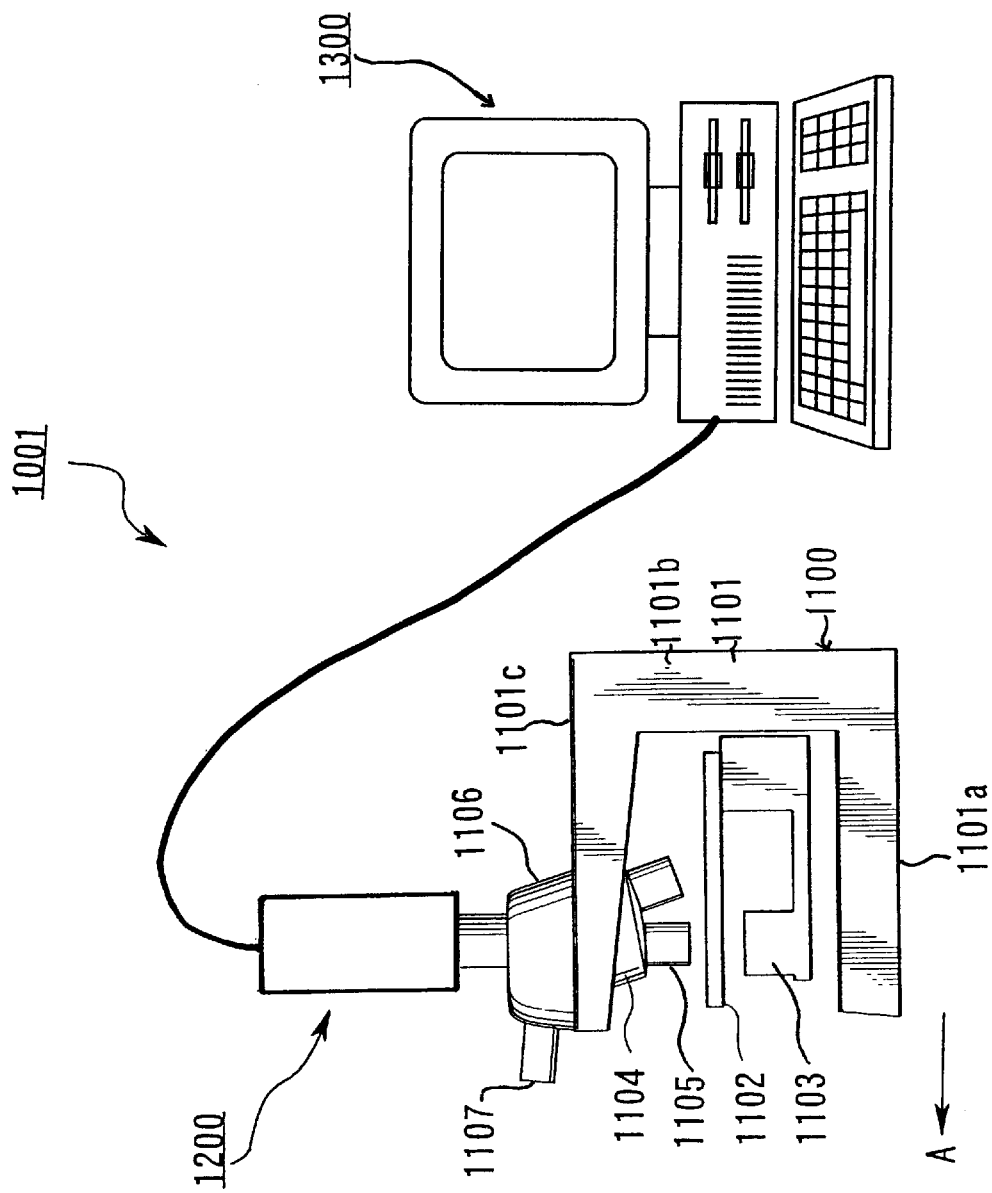
FIG. 20 is an external view illustrating the structure of the image-capturing device employed in a third embodiment.
Figure 21:
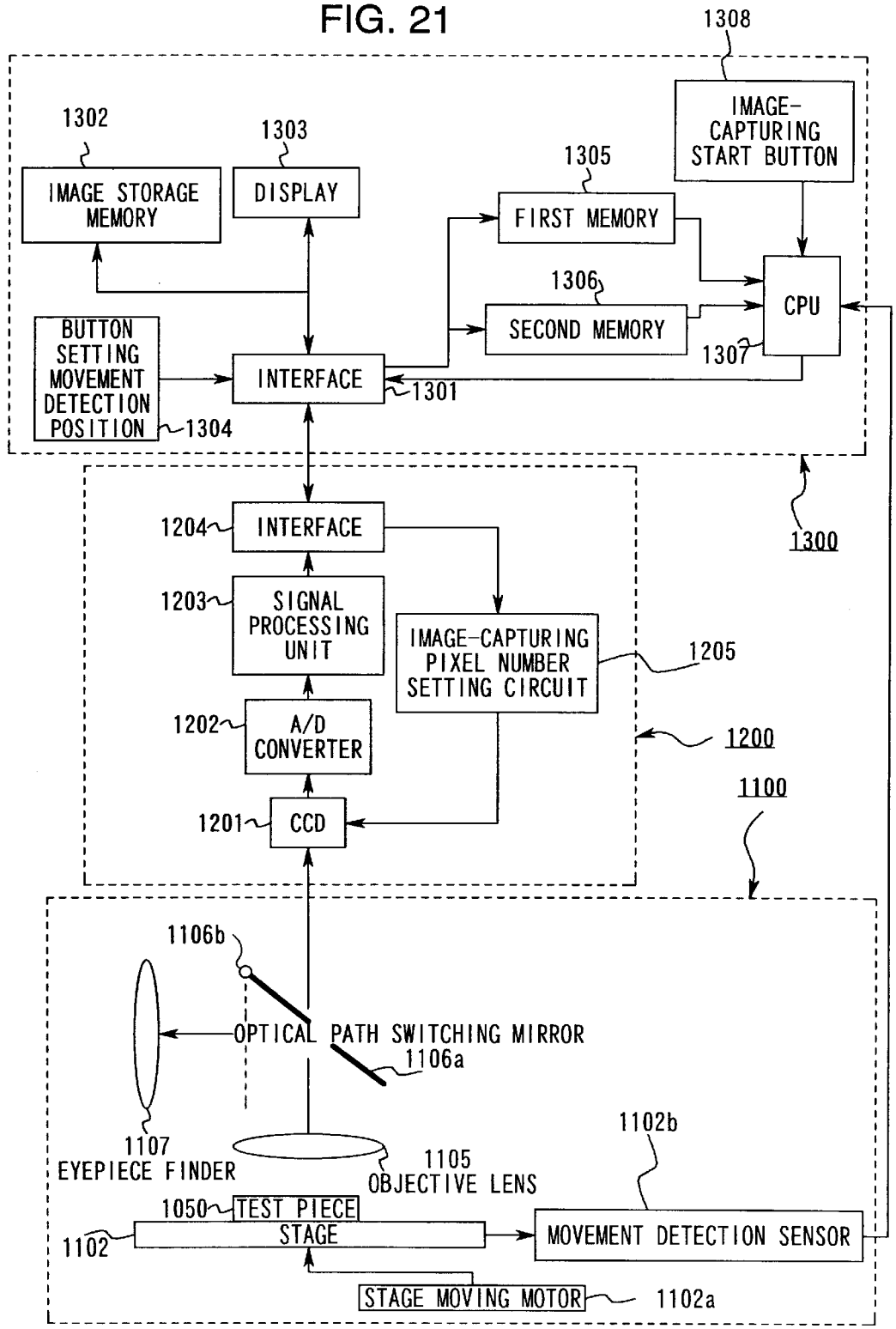
FIG. 21 is a block diagram illustrating the structure of the image-capturing device in the third embodiment.
Figure 22:
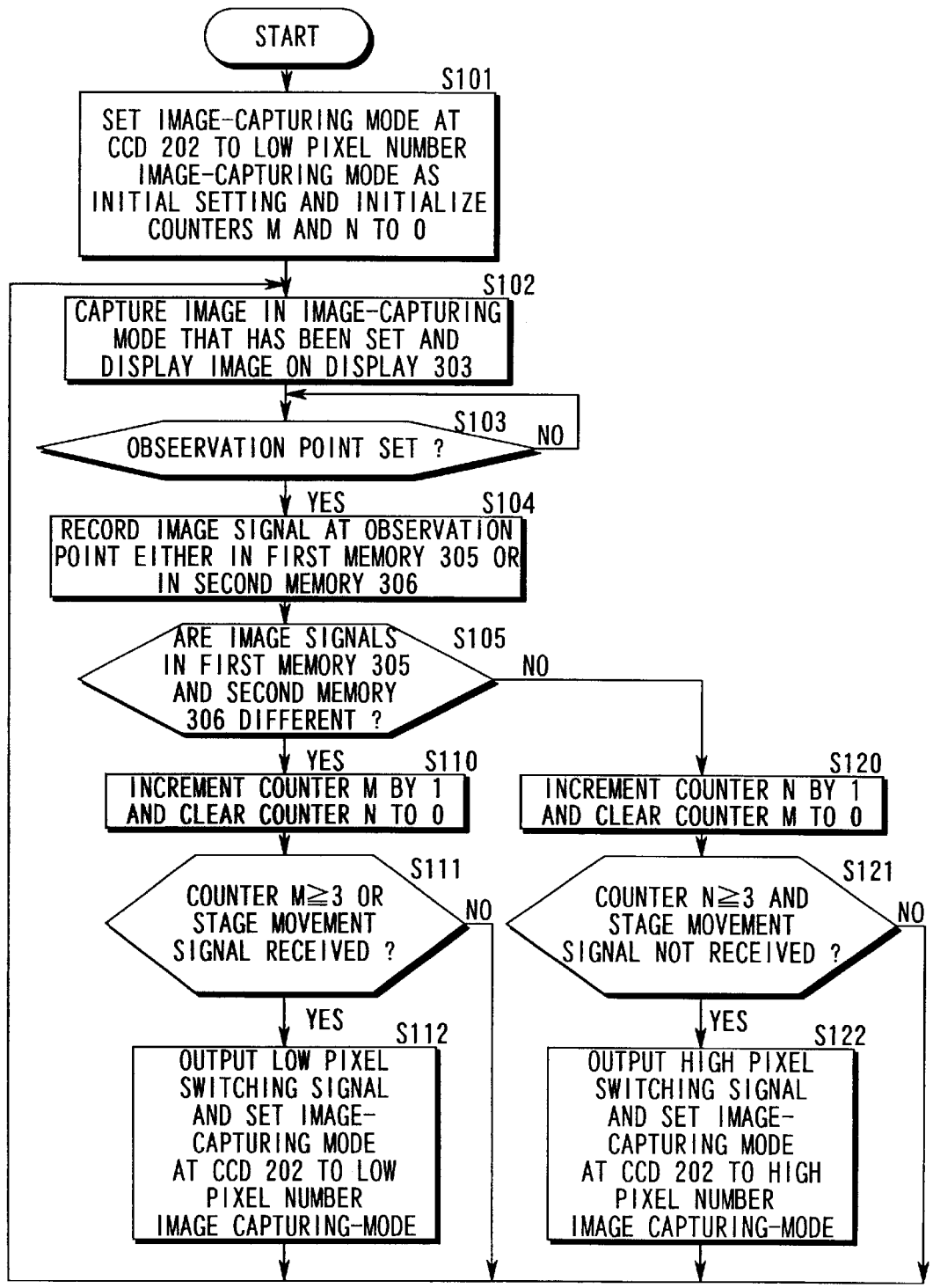
FIG. 22 is a flowchart illustrating a control procedure carried out for the image-capturing device in the third embodiment, with a single point set for examination.
Figure 23:
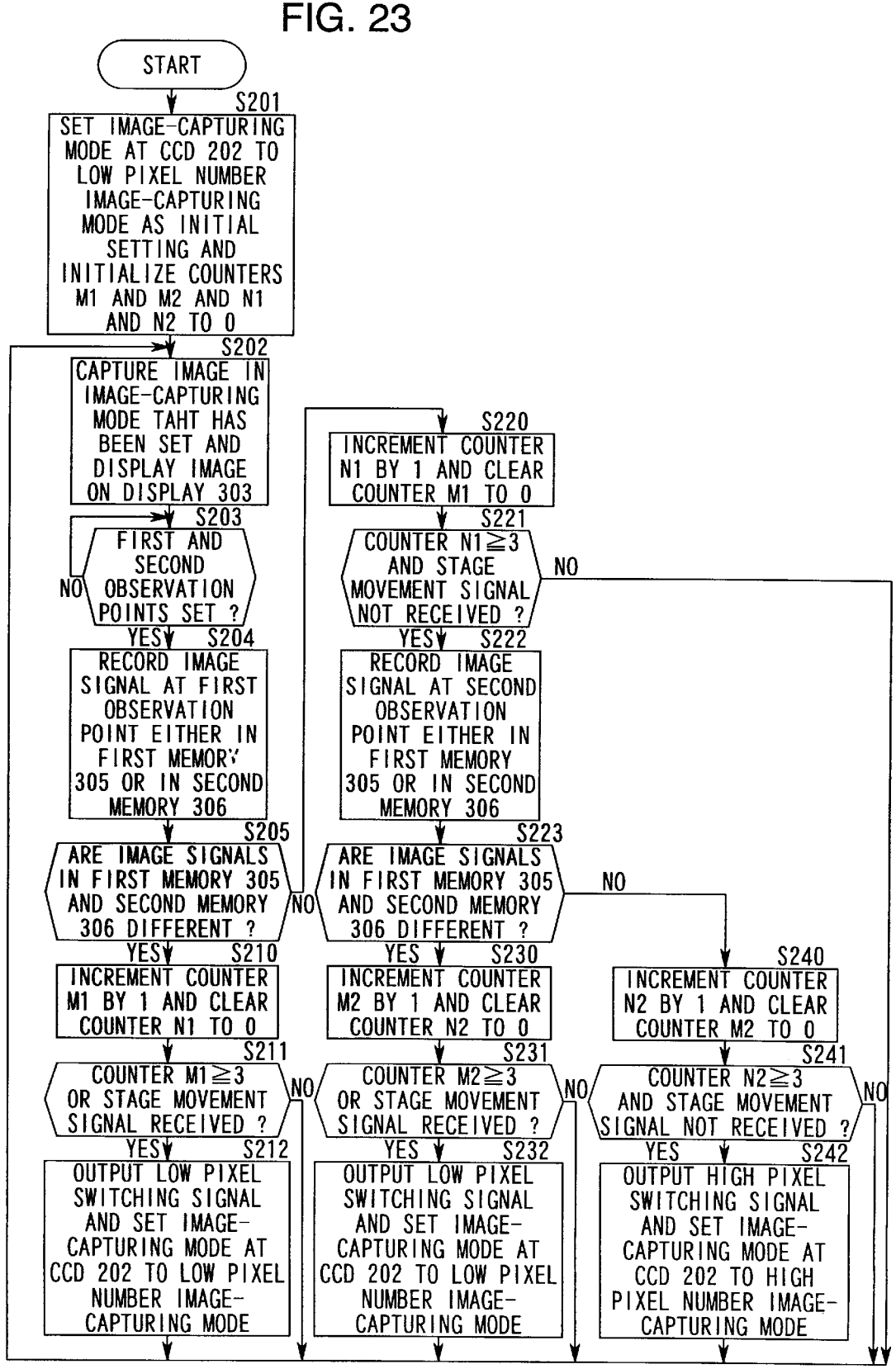
FIG. 23 is a flowchart illustrating a control procedure carried out for the image-capturing device in the third embodiment, with two points set for examination.

FIG. 20 is an external view of the structure of the image-capturing device employed in the third embodiment. FIG. 21 is a block diagram illustrating the structure of the image-capturing device employed in the third embodiment. FIG. 22 is a flowchart of a control procedure implemented at the image-capturing device employed in the third embodiment, with one point set for observation. FIG. 23 is a flowchart of the control procedure implemented at the image-capturing device in the third embodiment, with two points set for observation.

First, the structure of an image-capturing device 1001 employed in the third embodiment is explained in reference to FIG. 20 and FIG. 21.

As illustrated in FIG. 20, the image-capturing device 1001 in the third embodiment comprises a microscope 1100 that enlarges a test piece which constitutes the subject, a DSC 1200 that captures an image of the test piece and a personal computer (hereafter referred to in abbreviation as a PC) 1300 that is employed in display and recording of an image captured by the DSC 1200 and the operation of the image-capturing device 1001.

The microscope 1100 is constituted of a main body 1101, a stage 1102, an illuminating light source 1103, a revolver 1104, an objective lens 1105, a tube 1106 and an eyepiece finder 1107.

The main body 1101 supports the individual structures of the stage 1102, the illuminating light source 1103, the revolver 1104 and the tube 1106 which are to be detailed later. The main body 1101 is constituted of a base portion 1101a, a supporting column 1101b and an arm portion 1101c. The base portion 1101a supports the entire microscope 1100 and the supporting column 1101b is attached to its rear end with the direction indicated by the arrow A in FIG. 20 being the forward direction. The supporting column 1101b connects the base portion 1101a and the arm portion 1101c, with the stage 1102 and the illuminating light source 1103 attached to its front. The arm portion 1101c is mounted extending forward from the supporting column 1101b, and the tube 1106 is mounted at its upper surface toward the front with the revolver 1104 mounted at its lower surface toward the front. In addition, an opening (not shown) is formed at the arm portion 1101c to secure an optical path extending from the revolver 1104 to the tube 1106.

The stage 1102 is a table on which a test piece 1050 for examination is placed. The stage 1102 is capable of moving vertically to facilitate focusing adjustment. In addition, as illustrated in FIG. 21, the stage 1102 can be moved back and forth and to the left and right by a stage moving motor 1102a. Also, as illustrated in FIG. 21, the presence/absence of movement of the stage 1102 can be detected by a movement detection sensor 1102b. The movement detection sensor 1102b outputs a stage movement signal to a CPU 1307 which is to be detailed later when the stage 1102 has moved. Furthermore, the stage 1102 is provided with an opening (not shown), and with the test piece 1050 placed on the opening, the test piece 1050 can be illuminated by the illuminating light source 1103 which is to be detailed later.

The illuminating light source 1103 is a light source that emits illuminating light for illuminating the test piece 1050 on the stage 1102. Examples of the illuminating light source 1103 include a halogen lamp. The illuminating light source 1103 is positioned by ensuring that its illuminating light fully enters the entire entry opening at the objective lens 1105.

The revolver 1104 is a mounting member employed to mount the objective lens 1105 which is to be detailed later. The revolver 1104 mounts the objective lens 1105 so that the optical axis of the objective lens 1105 that is employed for examination intersects the stage 1105 vertically. In addition, the revolver 1104 is capable of mounting a plurality of different objective lenses and mounted objective lenses can be selected with the rotation of the revolver 1104.

The objective lens 1105 constitutes an optical system for enlarging the image of the test piece 1050 placed on the stage 1102. Light that has been transmitted through the objective lens 1105 travels through the revolver 1104 and the arm portion 1101c to enter the tube 1106.

The tube 1106 constitutes a switching optical system that selectively switches the destination of the optical path extending from the stage 1102, between the eyepiece finder 1107 and the DSC 1200 which are to be detail later. As illustrated in FIG. 21, the tube 1106 is internally provided with an optical path selection mirror 1106a which is to be detailed later. The optical path selection mirror 1106a is rotatably mounted at a rotating shaft 1106b. When the eyepiece finder 1107 is to be selected as the destination of the entering light, the optical path selection mirror 1106a rotates to a first position which is indicated by the solid line in FIG. 21 to select the optical path by reflecting the light. In addition, if the DSC 1200 is to be selected as the destination of the entering light, the optical path selection mirror 1106a rotates to a second position which is indicated by the dotted line in FIG. 21 to select the optical path by letting the light pass directly.

The eyepiece finder 1107 constitutes a finder optical system that allows the user to visually check the test piece 1050 on the stage 1102.

The DSC 1200 is an electronic camera that captures an image of the test piece 1050 placed on the stage 1102 and converts the image to an electrical signal for recording. As illustrated in FIG. 21, the DSC 1200 is constituted of a CCD 1201, an A/D converter 1202, a signal processing circuit 1203, a DSC interface 1204 and an image-capturing pixel number setting circuit 1205.

The CCD 1201 is a photoelectric conversion element that captures an image of the test piece 1050, converts the image to an analog image signal and output the signal. The CCD 1201 is provided by ensuring that its image-capturing plane is positioned on the image surface of the objective lens 1105. The number of pixels at the CCD 1201 that are to be utilized for image-capturing is controlled by the image-capturing pixel number setting circuit 1205 that is to be detailed later. The image signal achieved through the conversion performed at the CCD 1201 is output to the A/D converter 1202.

The A/D converter 1202 converts the image signal output by the CCD 1201, which is an analog signal, to a digital signal. The image signal having undergone digital conversion at the A/D converter 1202 is output to the signal processing circuit 1203.

The signal processing circuit 1203 performs digital signal processing including gamma conversion and white balance processing on the image signal output by the A/D converter 1202. The image signal having undergone the signal processing at the signal processing circuit 1203 is output to an image recording memory 1302 and a display 1303 via the DSC interface 1204 and a PC interface 1301 that are to be explained later.

The DSC interface 1204 is an interface provided to transmit and receive image signals and control signals to and from the PC 1300. The DSC interface 1204 is connected with the PC interface 1301 which is to be explained later.

The image-capturing pixel number setting circuit 1205 is provided to set the number of image-capturing pixels at the CCD 1201. The number of image-capturing pixels is set in response to a low pixel switching signal and a high pixel switching signal output by a CPU 1307 which is to be detailed later. By controlling the read out of the pixels at the CCD 1201, the image-capturing pixel number setting circuit 1205 sets one of the modes corresponding to varying numbers of pixels to be used for image-capturing, i.e., a high pixel number image-capturing mode and a low pixel number image-capturing mode. The high pixel number image-capturing mode and the low pixel number image-capturing mode achieve a relationship whereby the number of operating pixels is lower in the low pixel number image-capturing mode than in the high pixel number image-capturing mode. For instance, if the number of operating pixels in the high pixel number image-capturing mode is 480 pixels (down)×640 pixels (across), the number of operating pixels in the low pixel number image-capturing mode is 240 pixels (down)×320 pixels (across). Upon receiving the low pixel switching signal output by the CPU 1307 via the DSC interface 1204 and the PC interface 1301 which is to be detailed later, the image-capturing pixel number setting circuit 1205 sets the image-capturing mode at the CCD 1201 to the low pixel number image-capturing mode. If the image-capturing pixel number setting circuit 1205 receives the high pixel switching signal output by the CPU 1307 via the DSC interface 1204 and the PC interface 1301, on the other hand, it sets the image-capturing mode at the CCD 1201 to the high pixel number image-capturing mode.

The PC 1300 is employed in display and recording of an image captured by the DSC 1200 and in the operation of the image-capturing device 1001. As illustrated in FIG. 21, the PC 1300 comprises the PC interface 1301, the image recording memory 1302, the display 1303, an observation point setting button 1304, a first memory 1305, a second memory 1306, the CPU 1307 and an image-capturing start button 1308.

The PC interface 1301 is provided to transmit and receive image signals and control signals to and from the DSC 1200. The PC interface 1301 is connected to the DSC interface 1204. In addition, the PC interface 1301 outputs an image signal corresponding to the portion specified by the observation point setting button 1304 to be detailed later among image signals output by the signal processing circuit 1203 to the first memory 1305 and the second memory 1306 which are to be detailed later.

The image recording memory 1302 is provided to record image signals output by the signal processing circuit 1203. Examples of the image recording memory 1302 include a hard disk, a floppy disk, a semiconductor memory and a memory card. It is to be noted that the image recording memory 1302 may be of the type that can be attached to and detached from the PC 1300.

The display 1303 is a display device provided to display an image signal achieved through image-capturing. Examples of the display 1303 include a CRT and a liquid crystal display.

The observation point setting button 1304 is an input device operated by the user to set an observation point for detecting any movement in image signals achieved through image-capturing. A plurality of observation points may be set. The setting information with regard to the observation point input through the observation point setting button 1304 is output to the PC interface 1301.

The first memory 1305 and the second memory 1306 are provided to record image signals corresponding to the observation points set with the observation point setting button 1304 among the image signals output by the signal processing circuit 1203. The image signals corresponding to the observation points recorded in the first memory 1305 and the second memory 1306 are output to the CPU 1307. In addition, the timing with which image signals are input to the first memory 1305 and the second memory 1306 is controlled by the CPU 1307 which is to be described in detail later.

The CPU 1307 is a control circuit that controls the individual structures provided inside the PC 1300. The CPU 1307 alternately switches the recording destination for the image signals corresponding to the observation point output by the signal processing circuit 1203 between the first memory 1305 and the second memory 1306. Thus, the image signal at the most recent observation point and the image signal at the observation point for which image-capturing has been performed immediately before are recorded in the first memory 1305 and the second memory 1306 at all times. In addition, the CPU 1307 detects any movement or change in the image signals using the image signals at the observation points output from the first memory 1305 and the second memory 1306. The CPU 1307 extracts the R, G and B color components in the image signals at the observation points output by the first memory 1305 and the second memory 1306 and performs comparison for the individual color components. If the results of such comparison indicate a state 3 times or more consecutively in which the difference between color components of each of the R, G and B color components in image signals at the observation points is equal to or greater than 5%, the CPU 1307 outputs the low pixel switching signal to the image-capturing pixel number setting circuit 1205. In addition, if the results of the comparison indicate 3 times or more consecutively a state in which the difference between color components of each of the R, G and B color components in image signals at the observation points is equal to or less than 5%, the CPU 1307 outputs the high pixel switching signal to the image-capturing pixel number setting circuit 1205. The number of image-capturing pixels at the CCD 1201 is switched only when a state is indicated 3 times or more consecutively in order to reduce the effect of a momentary change in the image. In addition, if the CPU 1307 receives a stage movement signal output by the movement detection sensor 1102b, it outputs the low pixel switching signal to the image-capturing pixel number setting circuit 1205. Also, if the CPU 1307 receives the image-capturing start signal output by the image-capturing start button 1308, which is to be explained later, it prompts the DSC 1200 to perform an image-capturing operation and ensures that the image signals of the captured image are recorded in the image recording memory 1302.

The image-capturing start button 1308 is provided to start an image-capturing operation at the DSC 1200. When the image-capturing start button 1308 is operated by the user, it outputs an image-capturing start signal to the CPU 1307.

Next, the procedure of the control achieved by the CPU 1307 in the image-capturing device 1101 in the third embodiment is explained in reference to FIG. 22.

First, in step S101, the image-capturing mode at the CCD 1201 is set to the low pixel number image-capturing mode as the initial setting. In addition, 0 is set as the initial value at a counter M provided to count the number of times the CPU 1307 decides that image signals are different, and at a counter N provided to count the number of times the CPU 1307 decides that the image signals are identical. When the processing in step S101 is completed, the operation proceeds to step S102.

Next, in step S102, the CCD 1201 is prompted to engage in an image-capturing operation using the number of pixels that corresponds to the image-capturing mode that has been set and the image signal achieved through the image-capturing operation is displayed on a display 1212. When the processing in step S102 is completed, the operation proceeds to step S103.

Then, in step S103, a decision is made as to whether or not an observation point has been set through the observation point setting button 1304. If an observation point has been set, the operation proceeds to step S104, whereas if no observation point has been set, the operation remains in a standby state in step S103.

Next, in step S104, the image signal corresponding to the observation point set in step S103 is recorded in either the first memory 1305 or the second memory 1306 in which recording was not performed during the preceding operation. When the processing in step S104 is completed, the operation proceeds to step S105.

In step S105, the image signal at the observation point recorded in the first memory 1305 and the second memory 1306 are compared with each other with respect to the individual color components, i.e., the R, G and B color components. If the results of the comparison indicate that the difference between the image signal recorded in the first memory 1305 and the image signal recorded in the second memory 1306 exceeds 5%, it is decided that the image signal in the first memory 1305 and the image signal in the second memory 1306 are different signals before the operation proceeds to step S110. If, on the other hand, the difference between the image signal recorded in the first memory 1305 and the image signal recorded in the second memory 1306 is within 5%, it is decided that the image signal in the first memory 1305 and the image signal in the second memory 1306 are almost identical to each other, and the operation proceeds to step S120.

If it is decided in step S105 that the image signals are different from each other, the operation proceeds to step S110. In step S110, the value at the counter M is increased by 1 and the counter N is set to 0. When the processing in step S110 is completed, the operation proceeds to step S111.

Then, in step S111, by checking the value at the counter M and whether or not a stage movement signal has been received, a decision is made as to whether or not the image signal at the observation point indicates a moving state. If the value at the counter M is 3 or greater or if a stage movement signal has been received, it is decided that the image signal at the observation point indicates a moving state and the operation proceeds to step S112. If the value at the counter M is smaller than 3 or if no stage movement signal has been received, it is decided that the image signal at the observation point does not indicate a moving state and the operation proceeds to step S102 to repeat an image-capturing operation.

Next, in step S112, the image-capturing mode at the CCD1201 is set to the low pixel number image-capturing mode by outputting a low pixel switching signal to the pixel number setting circuit 1206. When the processing in step S112 is completed, the operation proceeds to step S102 to repeat an image-capturing operation.

If it is decided in step S105 that the image signals are almost identical to each other, the operation proceeds to step S120. In step S120, the value at the counter N is increased by 1 and the value at the counter M is set to 0. When the processing in step S120 is completed, the operation proceeds to step S121.

Next, by checking the value at the counter N and whether or not a stage movement signal has been received in step S121, a decision is made as to whether or not the image signal at the observation point indicates a stationary state. If the value at the counter N is equal to or greater than 3 and no stage movement signal has been received yet, it is decided that the image signal at the observation point indicates a stationary state and the operation proceeds to step S122. If the value at the counter N is smaller than 3 or if a stage movement signal has been received, it is decided that the image signal at the observation point does not indicate a stationary state and the operation proceeds to step S102 to repeat an image-capturing operation.

Then, in step S122, the image-capturing mode at the CCD 1201 is set to the high pixel image-capturing mode. When the processing in step S122 is completed, the operation proceeds to step S102 to repeat an image-capturing operation.

While only one point is set as an observation point in the control procedure explained above in reference to FIG. 22, FIG. 23 illustrates a control procedure adopted when two points are set as observation points.

First, in step S201, the image-capturing mode at the CCD 1201 is set to the low pixel number image-capturing mode as the initial setting. In addition, 0 is set as the initial value at counters M1 and M2 provided to count the number of times the CPU 1307 decides that the image signals are different and at counters N1 and N2 provided to count the number of times the CPU 1307 decides that the image signals are identical. When the processing in step S201 is completed, the operation proceeds to step S202.

Next, in step S202, the CCD 1201 is prompted to engage in an image-capturing operation using the number of pixels that corresponds to the image-capturing mode that has been set and the image signal achieved through the image-capturing operation is displayed on the display 1212. When the processing in step S202 is completed, the operation proceeds to step S203.

Then, in step S203, a decision is made as to whether or not a first observation point and a second observation point have been set through the observation point setting button 1304. If observation points have been set, the operation proceeds to step S204, whereas if no observation points have been set, the operation remains in a standby state in step S203.

Next, in step S204, the image signal corresponding to the first observation point set in step S203 is recorded in either the first memory 1305 or the second memory 1306 in which recording was not performed during the preceding operation. When the processing in step S204 is completed, the operation proceeds to step S205.

In step S205, image signals at the first observation point recorded in the first memory 1305 and the second memory 1306 are compared with each other with respect to he individual color components, i.e., the R, G and B color components. If the results of the comparison indicate that the difference between the image signal recorded in the first memory 1305 and the image signal recorded in the second memory 1306 exceeds 5%, it is decided that the image signal in the first memory 1305 and the image signal in the second memory 1306 are different signals before the operation proceeds to step S210. If, on the other hand, the difference between the image signal recorded in the first memory 1305 and the image signal recorded in the second memory 1306 is within 5%, it is decided that the image signal in the first memory 1305 and the image signal in the second memory 1306 are almost identical to each other, and the operation proceeds to step S220.

If it is decided in step S205 that the image signals are different from each other, the operation proceeds to step S210. In step S210, the value at the counter M1 is increased by 1 and the counter N1 is set to 0. When the processing in step S210 is completed, the operation proceeds to step S211.

Then, in step S211, by checking the value at the counter M1 and whether or not a stage movement signal has been received, a decision is made as to whether or not the image signal at the observation point indicates a moving state. If the value at the counter M1 is 3 or greater or if a stage movement signal has been received, it is decided that the image signal at the observation point indicates a moving state and the operation proceeds to step S212. If the value at the counter M1 is smaller than 3 and no stage movement signal has been received, it is decided that the image signal at the observation point does not indicate a moving state and the operation proceeds to step S202 to repeat an image-capturing operation.

Next, in step S212, the image-capturing mode at the CCD1201 is set to the low pixel number image-capturing mode by outputting a low pixel switching signal to the pixel number setting circuit 1206. When the processing in step S212 is completed, the operation proceeds to step S202 to repeat an image-capturing operation.

If it is decided in step S205 that the image signals are almost identical to each other, the operation proceeds to step S220. In step S220, the value at the counter N1 is increased by 1 and the value at the counter M1 is set to 0. When the processing in step S220 is completed, the operation proceeds to step S221.

Next, by checking the value at the counter N1 and whether or not a stage movement signal has been received in step S221, a decision is made as to whether or not the image signal at the observation point indicates a stationary state. If the value at the counter N1 is equal to or greater than 3 and no stage movement signal has been received yet, it is decided that the image signal at the observation point indicates a stationary state and the operation proceeds to step S222. If the value at the counter N1 is smaller than 3 or if a stage movement signal has been received, it is decided that the image signal at the observation point does not indicate a stationary state and the operation proceeds to step S202 to repeat an image-capturing operation.

Then, in step S222, the image signal at the second observation point set in step S203 is recorded either in the first memory 1305 or the second memory 1306 in which no recording was performed in the previous operation. When the processing in step S222 is completed, the operation proceeds to step S223.

In step S223, image signals at the second observation point recorded in the first memory 1305 and the second memory 1306 are compared with each other with respect to the individual color components, i.e., the R, G and B color components. If the results of the comparison indicate that the difference between the image signal recorded in the first memory 1305 and the image signal recorded in the second memory 1306 exceeds 5%, it is decided that the image signal in the first memory 1305 and the image signal in the second memory 1306 are different signals before the operation proceeds to step S230. If, on the other hand, the difference between the image signal recorded in the first memory 1305 and the image signal recorded in the second memory 1306 is within 5%, it is decided that the image signal in the first memory 1305 and the image signal in the second memory 1306 are almost identical to each other, and the operation proceeds to step S240.

If it is decided in step S223 that the image signals are different from each other, the operation proceeds to step S230. In step S230, the value at the counter M2 is increased by 1 and the counter N2 is set to 0. When the processing in step S230 is completed, the operation proceeds to step S231.

Then, in step S231, by checking the value at the counter M2 and whether or not a stage movement signal has been received, a decision is made as to whether or not the image signal at the observation point indicates a moving state. If the value at the counter M2 is 3 or greater or if a stage movement signal has been received, it is decided that the image signal at the observation point indicates a moving state and the operation proceeds to step S232. If the value at the counter M2 is smaller than 3 and no stage movement signal has been received, it is decided that the image signal at the observation point does not indicate a moving state and the operation proceeds to step S202 to repeat an image-capturing operation.

Next, in step S232, the image-capturing mode at the CCD1201 is set to the low pixel number image-capturing mode by outputting a low pixel switching signal to the pixel number setting circuit 1206. When the processing in step S232 is completed, the operation proceeds to step S202 to repeat an image-capturing operation.

If it is decided in step S223 that the image signals are almost identical to each other, the operation proceeds to step S240. In step S240, the value at the counter N2 is increased by 1 and the value at the counter M2 is set to 0. When the processing in step S240 is completed, the operation proceeds to step S241.

Next, by checking the value at the counter N2 and whether or not a stage movement signal has been received in step S241, a decision is made as to whether or not the image signal at the observation point indicates a stationary state. If the value at the counter N2 is equal to or greater than 3 and no stage movement signal has been received yet, it is decided that the image signal at the observation point indicates a stationary state and the operation proceeds to step S242. If the value at the counter N2 is smaller than 3 or if a stage movement signal has been received, it is decided that the image signal at the observation point does not indicate a stationary state and the operation proceeds to step S202 to repeat an image-capturing operation.

Next, by outputting a high pixel switching signal to the pixel number setting circuit 1206 in step S242, the image-capturing mode at the CCD 1201 is set to the high pixel number image-capturing mode. When the processing in step S242 is completed, the operation proceeds to step S202 to repeat the image-capturing operation.

It is to be noted that in the third embodiment, the decision-making in regard to the presence/absence of movement is implemented by ascertaining the difference independently at each observation point even when a plurality of observation points are set. However, the decision-making in regard to the presence/absence of movement may be performed by calculating the average value of differences at a plurality of observation points or by calculating the total of differences at a plurality of observation points.

In addition, while the high pixel number image-capturing mode is set in the third embodiment if all the observation points are decided to be in a stationary state in the decision-making with regard to the presence/absence of movement with a plurality of observation points set, the high pixel number image-capturing mode may be set as long as a stationary state is detected at any one of the plurality of observation points that have been set.

Furthermore, in regard to the threshold value used for the decision-making on the difference between image signals, the decision-making may be performed based upon whether or not the difference is within a specific ratio as in the third embodiment or the decision-making may be performed based upon whether or not the difference is under a specific value. For instance, if the signal levels of image signals are represented through 8-bit resolution ranging from 0 to 255, the decision-making may be performed based upon whether or not the difference is within ±5. Alternatively, the intensities of the individual color components, i.e., the R, G and B color components, extracted from image signals at the observation points may be normalized and then the histogram distributions of the intensities may be determined so that the fluctuations in the histogram distributions can be utilized for decision-making.

Moreover, while the explanation has been given on the third embodiment on the assumption that the DSC 1200 and the PC 1300 are separate structures, the PC 1300 may be provided internally within the DSC 1200 so that the DSC and the microscope constitute a system.

What is claimed is:

1. A section image obtaining apparatus that obtains a section image of a subject, comprising:
    an image-capturing device that captures an image of the subject and generates image data corresponding to the subject whose image has been captured, said image-capturing device being provided with an image-capturing element constituted of a plurality of pixels that are two-dimensionally arrayed;
    a section specifying device that specifies a vertical section extending in a direction perpendicular to an image-capturing surface of said image-capturing device and specifies the vertical section at the subject;
    a distance adjusting device that adjusts a distance between the subject and said image-capturing device in order to focus on a given position at the subject when capturing an image of the subject at said image-capturing device;
    a section image processing device that processes the image data generated by said image-capturing device; and
    a microscope provided with an objective lens between the subject and said image-capturing device that enlarges an image of the subject by a magnification power of M, wherein:
        said image-capturing device captures an image of the subject for each distance resulting from an adjustment made by said distance adjusting device;
        said section image processing device extracts image data at a portion intersecting the section specified by said section specifying device among the image data generated by said image-capturing device every time an image of the subject is captured by said image-capturing device, and obtains a section image of the subject by synthesizing the image data thus extracted;
        said distance adjusting device adjusts the distance between the subject and said objective lens;
        said distance adjusting device adjusts a distance between the subject and said section image obtaining apparatus in units of distance equaling (a length of one side of a pixel/M); and
        said section image processing device extracts image data at pixels corresponding to the position at which the section specified by said section specifying device is intersected.

2. A section image obtaining apparatus that obtains a section image of a subject, comprising:
    an image-capturing device that captures an image of the subject and generates image data corresponding to the subject whose image has been captured, said image-capturing device being provided with an image-capturing element constituted of a plurality of pixels that are two-dimensionally arrayed;
    a section specifying device that specifies a vertical section extending in a direction perpendicular to an image-capturing surface of said image-capturing device and specifies the vertical section at the subject;
    a distance adjusting device that adjusts a distance between the subject and said image-capturing device in order to focus on a given position at the subject when capturing an image of the subject at said image-capturing device;
    a section image processing device that processes the image data generated by said image-capturing device; and
    a microscope provided with an objective lens between the subject and said image-capturing device that enlarges an image of the subject by a magnification power of M, wherein:
        said image-capturing device captures an image of the subject for each distance resulting from an adjustment made by said distance adjusting device;
        said section image processing device extracts image data at a portion intersecting the section specified by said section specifying device among the image data generated by said image-capturing device every time an image of the subject is captured by said image-capturing device, and obtains a section image of the subject by synthesizing the image data thus extracted;
        said distance adjusting device adjusts the distance between the subject and said objective lens;
        said distance adjusting device adjusts a distance between the subject and said section image obtaining apparatus in units of distance J; and
        said section image processing device extracts image data at pixels corresponding to the position at which the section specified by said section specifying device is intersected, and performs enlargement processing at a magnification power of (J/(length of one side of pixel/M)) to synthesize the extracted image data.

* * * * *